(12) United States Patent
Kuhner-Stout et al.

(10) Patent No.: US 11,849,777 B2
(45) Date of Patent: Dec. 26, 2023

(54) ENERGIZING GARMENT

(71) Applicants:Emeline Kuhner-Stout, Houston, TX (US); Myron Stout, Houston, TX (US)

(72) Inventors: Emeline Kuhner-Stout, Houston, TX (US); Myron Stout, Houston, TX (US)

(*) Notice: Subject to any disclaimer, the term of this patent is extended or adjusted under 35 U.S.C. 154(b) by 715 days.

(21) Appl. No.: 17/042,741

(22) PCT Filed: Mar. 28, 2019

(86) PCT No.: PCT/US2019/024690
§ 371 (c)(1),
(2) Date: Sep. 28, 2020

(87) PCT Pub. No.: WO2019/191498
PCT Pub. Date: Oct. 3, 2019

(65) Prior Publication Data
US 2021/0093023 A1    Apr. 1, 2021

Related U.S. Application Data

(60) Provisional application No. 62/649,567, filed on Mar. 28, 2018.

(51) Int. Cl.
*A41D 13/00*    (2006.01)
*A41B 1/00*    (2006.01)
(Continued)

(52) U.S. Cl.
CPC ............ *A41D 13/0015* (2013.01); *A41B 1/00* (2013.01); *A41D 1/08* (2013.01); *A41D 13/02* (2013.01);
(Continued)

(58) Field of Classification Search
CPC ......... A61H 7/00–2007/009; A61H 15/00–02; A61H 39/00–086; A61H 2201/165; A41D 2400/322
See application file for complete search history.

(56) References Cited

U.S. PATENT DOCUMENTS 4,121,582 A    10/1978 Remiro
4,810,559 A    3/1989 Fortier et al.
(Continued)

FOREIGN PATENT DOCUMENTS

DE    19825693 A1    12/1999
DE    102012101837    1/2014
(Continued)

OTHER PUBLICATIONS

Response to UK Intellectual Property Office Examination Report, dated Feb. 1, 2023, pp. 1-49.
(Continued)

*Primary Examiner* — Valerie L Woodward
(74) *Attorney, Agent, or Firm* — J L Salazar

(57) ABSTRACT

The present disclosure relates to energizing garments wearable by a user. The energizing garment is provided with compressive material and fingers (e.g., watershed fingers and/or massage (non-watershed) fingers) that can be positioned about the user's body to provide a combination of compression and penetrating massage to tissues that are oriented relative to watersheds of the user. The compressive material and fingers may be sized, shaped, oriented, or arranged in patterns to strategically energize the tissues of the user to release fluids, such as lymph, interstitial fluids, and/or blood, along or across the watersheds.

23 Claims, 20 Drawing Sheets

(51) Int. Cl.
*A41D 1/08* (2018.01)
*A41D 13/02* (2006.01)
*A41H 43/00* (2006.01)
*A61F 13/08* (2006.01)
*A61H 7/00* (2006.01)

(52) U.S. Cl.
CPC ............. *A41H 43/00* (2013.01); *A61F 13/08* (2013.01); *A61H 7/002* (2013.01); *A41D 2400/322* (2013.01); *A61H 2201/165* (2013.01); *A61H 2201/1692* (2013.01); *A61H 2209/00* (2013.01)

(56) References Cited

U.S. PATENT DOCUMENTS

| | | |
|---|---|---|
| 5,794,266 A | 8/1998 | Han |
| 6,032,296 A | 3/2000 | Kelly et al. |
| 6,138,281 A | 10/2000 | Chiaruttini |
| 6,361,397 B1 | 3/2002 | Mankovitz et al. |
| 6,596,289 B1 | 7/2003 | Pugliese |
| 6,852,089 B2 | 2/2005 | Kloecker et al. |
| 7,135,007 B2 | 11/2006 | Scott et al. |
| 9,756,881 B2 | 9/2017 | L'eprevier et al. |
| 10,420,694 B2 | 9/2019 | Barker |
| 2005/0113729 A1 | 5/2005 | Scott et al. |
| 2007/0033696 A1* | 2/2007 | Sellier .................. A61H 7/001 2/69 |
| 2008/0134406 A1 | 6/2008 | Shih et al. |
| 2008/0208296 A1 | 8/2008 | Smith et al. |
| 2011/0191931 A9 | 8/2011 | Sellier |
| 2011/0208104 A1 | 8/2011 | Sellier |
| 2012/0089058 A1 | 4/2012 | Ellis |
| 2014/0142614 A1 | 5/2014 | Gallagher |
| 2014/0148741 A1 | 5/2014 | Moran |
| 2015/0133836 A1 | 5/2015 | Pollock |
| 2015/0173428 A1 | 6/2015 | Langer et al. |
| 2015/0366735 A1* | 12/2015 | Barker .................. A61F 13/143 601/84 |
| 2019/0021939 A1* | 1/2019 | Forbes .................. A61H 7/001 |

FOREIGN PATENT DOCUMENTS

| | | |
|---|---|---|
| EP | 2904999 A1 | 8/2015 |
| GB | 2587129 A | 3/2021 |
| WO | 2013190201 A1 | 12/2013 |

OTHER PUBLICATIONS

Response to UK Intellectual Property Office Examination Report, dated Aug. 11, 2022, pp. 1-13.
Response to UK Intellectual Property Office Examination Report, dated Nov. 21, 2022, pp. 1-18.
UK Intellectual Property Office Examination Report under section 18(3), dated Nov. 21, 2022, pp. 1-5.
UK Intellectual Property Office Examination Report under section 18(3), dated Jan. 3, 2023, pp. 1-4.
UK Intellectual Property Office Intention to Grant under section 18(4), dated Mar. 17, 2023, pp. 1-2.
UK Intellectual Property Office Examination Report under section 8(3), dated Apr. 25, 2022, pp. 1-8.
UK Intellectual Property Office Examination Report under section 8(3), dated Dec. 1, 2021, pp. 1-2.
UK Response to Examination Report, dated Mar. 23, 2022, pp. 1-11.
Gallagher, Portable Mat, US Design Patent No. D754359 S, issued Apr. 19, 2016.
Gilbert Forbes, Lymphatics of the Skin, With a Note on Lymphatic Watershed Areas, J Anat. Apr. 1938; 72(Pt 3): pp. 399-410.
WIPO, International Search Report & Written Opinion, dated Jun. 14, 2019, pp. 1-12.

* cited by examiner

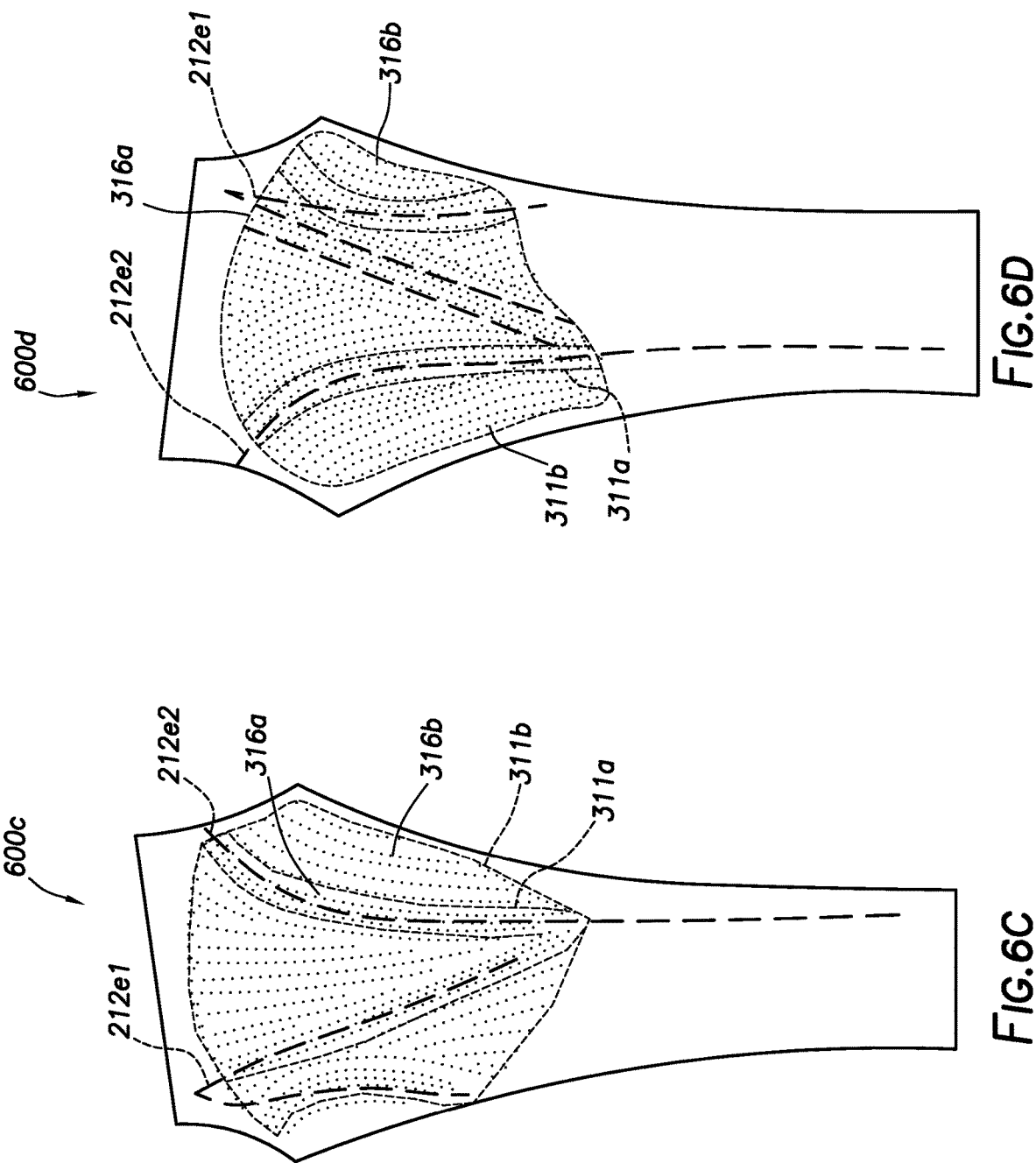

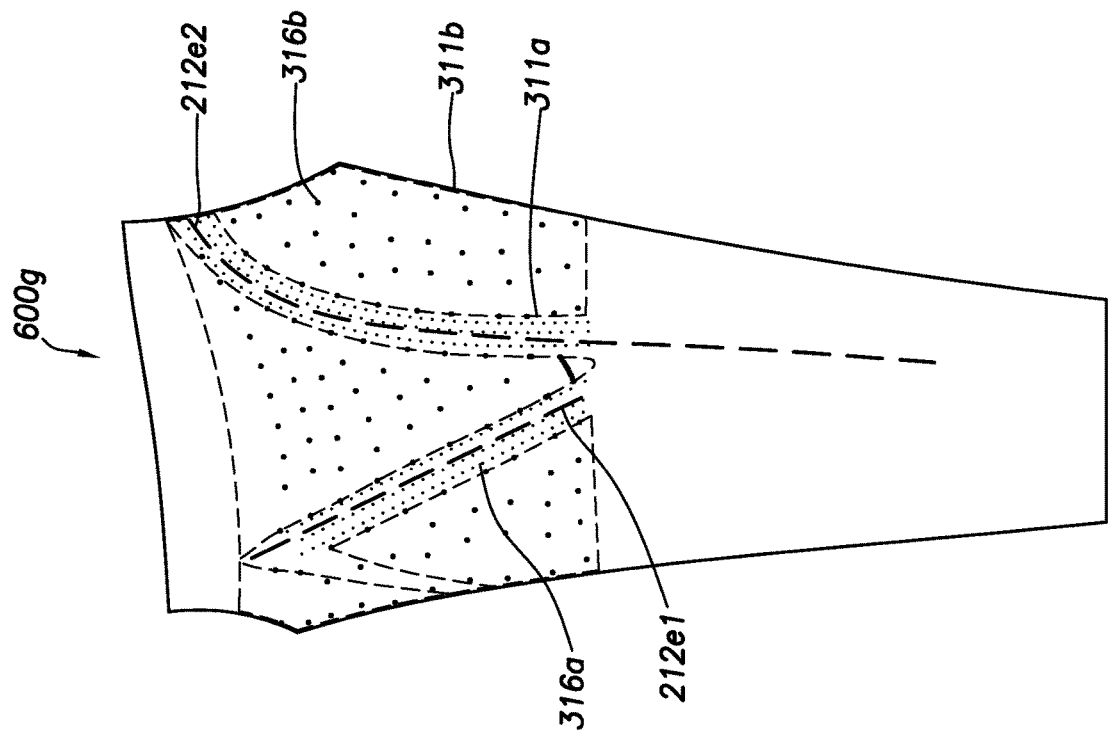
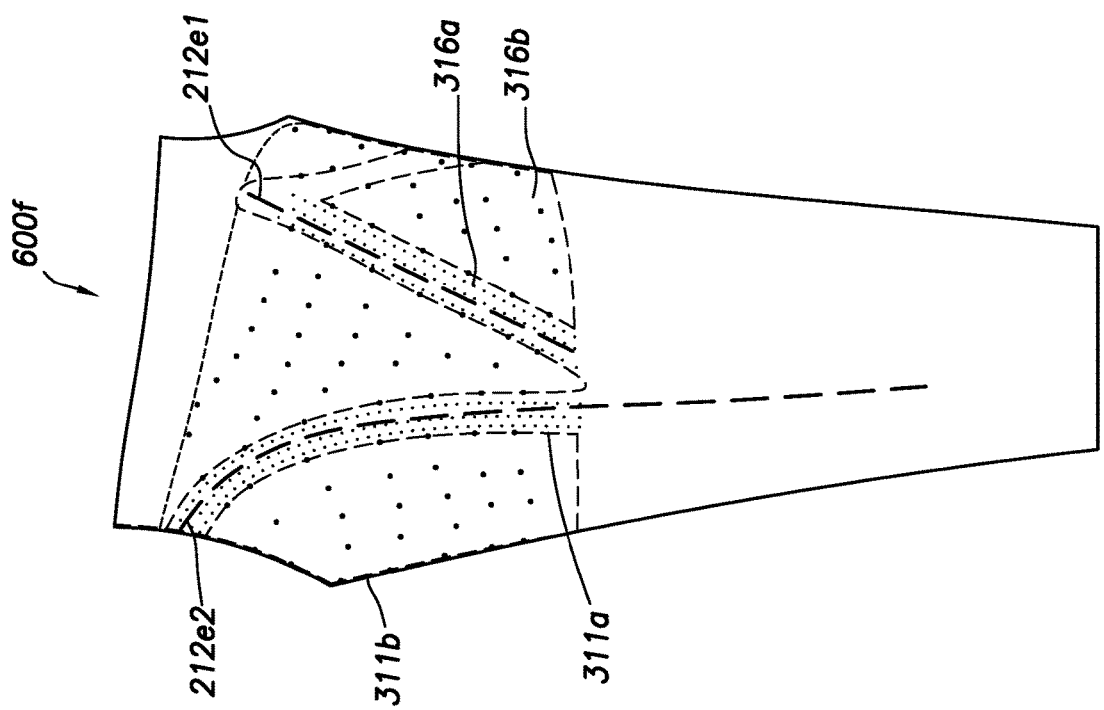

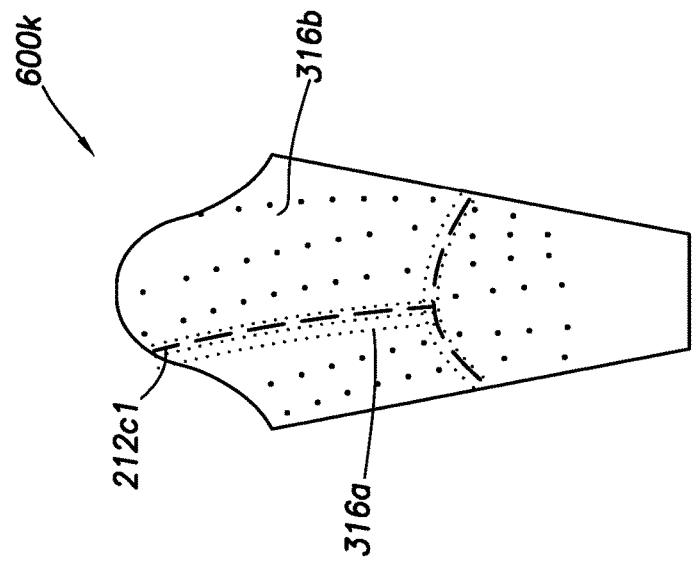
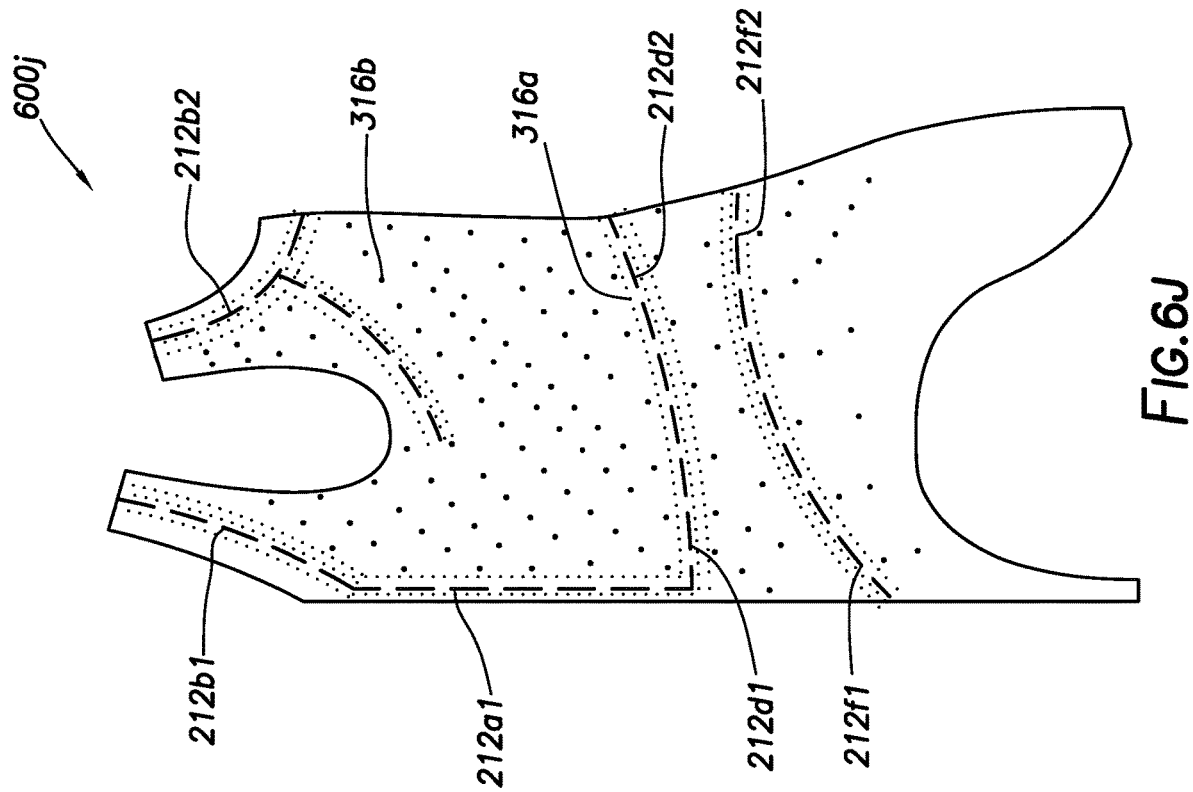

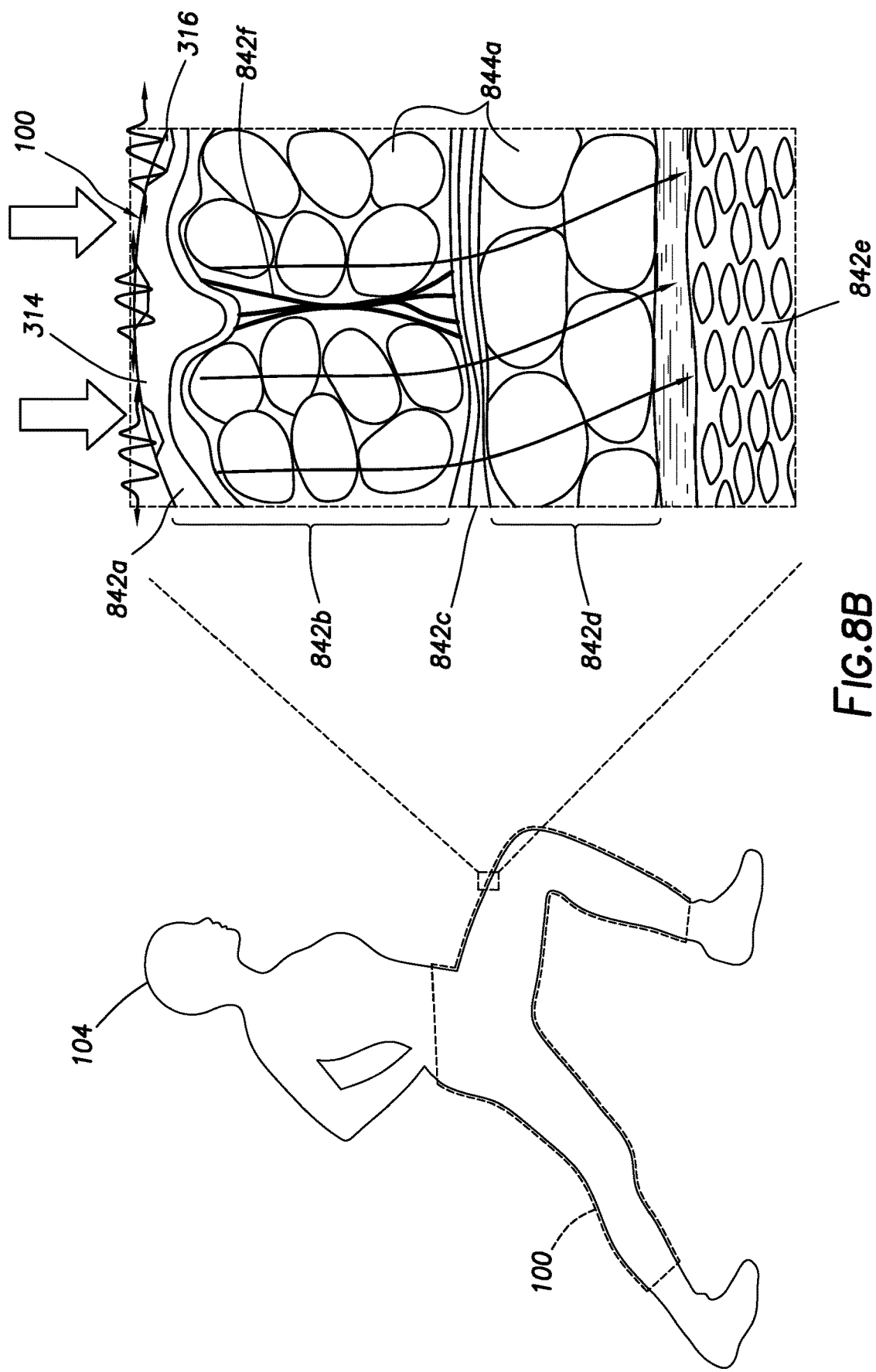

ENERGIZING GARMENT

CROSS-REFERENCE TO RELATED APPLICATION

This application claims the benefit of U.S. Provisional Application Ser. No. 62/649,567, the entire contents of which is hereby incorporated by reference herein.

BACKGROUND

The present disclosure relates generally to treatment of human tissues. More specifically, the present disclosure relates to garments for treating human tissues to encourage fluid flow through the body.

The human vascular circulatory system includes a lymphatic system made up of a complex network of lymphatic vessels, lymph nodes, and tissues that function to transport lymph through the body. The lymphatic system is fundamentally important to overall health for at least three reasons: first, the lymphatic system controls the absorbance of nutrients including proteins and lipids from blood vasculature into peripheral tissues; second, lymphatic vessels route immune cells from peripheral tissues into lymph nodes for immune protection; and lastly, the lymphatic system maintains fluid homeostasis in the interstitium by regulating lymph transport.

Impairment of lymphatic functioning, e.g., inadequate lymph transport or inadequate interstitial fluid absorption, may lead to a higher prevalence of gynoid lipodystrophy (GLD), commonly known as "cellulite," an aesthetically unacceptable problem for many post-adolescent women. More acute impairment of lymphatic functioning may lead to medical disorders, such as edema, impaired immunity, and fibrosis.

SUMMARY

The following presents a general summary of several aspects of the disclosure in order to provide a basic understanding of the disclosure. This summary is provided to introduce a selection of concepts that are further described below in the detailed description. This summary is not an extensive overview of the disclosure nor is it intended to identify key or critical elements or to delineate the scope of the claims. This summary is also not intended to identify optimal features of the claimed subject matter, nor is it intended to be used as an aid in limiting the scope of the claimed subject matter. The following summary merely presents some concepts of the disclosure in a general form as a prelude to the more detailed description that follows.

In at least one aspect, the disclosure relates to an energizing garment for treating tissues of a user. The garment comprises a compressive material, massage fingers, and watershed fingers. The compressive material is configured to be worn by the user. The compressive material is shaped to apply a compressive force to the skin of the user. When worn by a user, the compressive material has at least one watershed portion positioned about at least one watershed of the user and at least one massage (non-watershed) portion positioned about at least one non-watershed portion of the user. The watershed fingers are secured to at least a portion of the at least one watershed portion of the compressive material. The watershed fingers are arranged in a watershed pattern oriented to engage at least one watershed of the user and to encourage fluid flow along or across the at least one watershed. The massage fingers are secured to at least a portion of the at least one non-watershed portion of the compressive material. The massage fingers are arranged in a massage pattern oriented to define a fluid path for passage of fluid from the at least one non-watershed portion to the at least one watershed whereby tissues of the user are energized to release the fluid.

The massage fingers may have tips shaped to penetratingly massage the non-watershed portions. The material may comprise material portions comprising at least one of multiple layers, multiple pieces patched together, integral portions, the same portions, at least one different portion, and combinations thereof. The massage pattern may be shaped to apply a compressive force to the at least one non-watershed portions. The massage pattern may be shaped to apply compressive forces to target areas of the user. The massage fingers may be positioned along target areas of the user comprising concentrations of cellulite, fat, muscle, veins, and combinations thereof.

In another aspect, the disclosure relates to a method of making a garment for treating tissues of a user. The method comprises providing a compressive material having elasticity;—shaping the compressive material into a material pattern conforming to a portion of body of a user;—securing watershed fingers to the compressive material along at least one watershed region of the user in a watershed pattern corresponding to the watershed regions of body and shaped to engage the watershed and encourage fluid flow along the at least one watershed; and securing massage fingers to the compressive material along at least one non-watershed portion of the user in a massage pattern defining a fluid path configured to encourage passage of fluid from the non-watershed portions to the at least one watershed region.

The method may also include defining the material pattern such that the compressive material applies a compressive force against skin of the body; defining the material pattern, the watershed pattern, and the non-watershed pattern such that the compressive material applies a compressive force to drive the watershed fingers and the massage fingers against skin of the body and into underlying tissues therebelow; defining the material pattern, the watershed pattern, and the non-watershed pattern such that the compressive material applies an energizing force to drive the watershed fingers and the massage fingers against skin of the body and agitate underlying tissues therebelow during movement of the user; and defining the watershed pattern and the non-watershed pattern may to energize tissues of the user to motivate interstitial fluid flow and to smooth cellulite.

In at least one aspect, the disclosure relates to an energizing garment, comprising a compressive material, watershed fingers, and massage fingers. The compressive material is configured to be worn by the user. The compressive material is shaped to apply a compressive force to skin of the user. The compressive material has at least one watershed portion positioned about at least one watershed of the user and at least one non-watershed portion positioned about at least one non-watershed region of the user. The watershed fingers are secured to the at least one watershed portion of the compressive material. The watershed fingers are arranged in a watershed pattern oriented to engage at least a portion of the watershed of the user and to encourage fluid flow about the at least one watershed. The massage fingers secured to the at least one non-watershed portion of the compressive material. The massage fingers are arranged in a massage pattern defining a fluid path for passage of fluid from the non-watershed region to the at least one watershed whereby tissues of the user are energized to release the fluid.

The watershed pattern may have a shape similar to the shape of the watershed. The massage pattern may be similar to the watershed pattern, and the massage fingers may be positioned along the massage pattern a distance from the watershed. The massage pattern may be oriented to the watershed, and the massage fingers may be positioned along the massage pattern a distance from the watershed. The massage fingers may have tips shaped to penetratingly massage the at least one non-watershed region of the user. The compressive material may comprise material portions comprising at least one of multiple layers, multiple pieces patched together, integral portions, similar portions, at least one different portion, and combinations thereof. The massage pattern may be shaped to apply a compressive force to the at least one non-watershed region of the user. The massage pattern may be shaped to apply compressive forces to target areas of the user. The massage fingers may be positioned along target areas of the user comprising concentrations of cellulite, fat, muscle, veins, and combinations thereof. The compressive material may be shaped to form one of a shirt, pants, shorts, jumpsuit, and leotard.

In another aspect, the disclosure relates to an energizing garment comprising a compressive material, watershed fingers, and massage fingers. The compressive material is shaped to conform to a body of the user. The compressive material has an elasticity to apply a compressive force against the body of the user when worn by the user. The compressive material having at least one watershed portion positioned about at least one watershed of the user and at least one non-watershed portion positioned about at least one non-watershed region of the user. The watershed fingers secured to the at least one watershed portion of the compressive material to compressively engage at least a portion of the watershed of the user and to encourage flow through the at least one watershed. The massage fingers secured to the at least one non-watershed portion of the compressive material to massagingly engage at least a portion of the non-watershed portion of the compressive material and to encourage fluid flow towards the at least one watershed whereby the tissues of the user are energized to release fluid and smooth skin of the user.

The massage fingers are positioned in a massage pattern defining a fluid pathway for encouraging the fluid flow towards or away from the at least one watershed. The massage fingers extend a distance below the compressive material to penetratingly engage the user and to compress layers below a surface of the skin of the user when the energizing garment is worn. The massage fingers may comprise a plastic secured to the compressive material. The massage fingers are positioned along one of: an inner surface of the compressive material, and between layers of the compressive material.

Finally, in another aspect, the disclosure relates to a method of making an energizing garment for treating tissues of a user. The method comprises providing a compressive material having elasticity, cutting the compressive material into a material pattern conforming to a body of the user, securing watershed fingers to the compressive material in a watershed pattern, the watershed pattern corresponding to watershed regions of body, and securing massage fingers to the compressive material in a non-watershed pattern, the non-watershed pattern corresponding to non-watershed regions of body.

The method further comprises defining the material pattern such that the compressive material applies a compressive force against skin of the body; defining the material pattern, the watershed pattern, and the non-watershed pattern such that the compressive material applies a compressive force to drive the watershed fingers and the massage fingers against skin of the body and into underlying tissues therebelow; defining the material pattern, the watershed pattern, and the non-watershed pattern defined such that the compressive material applies an energizing force to drive the watershed fingers and the massage fingers against skin of the body and agitate underlying tissues therebelow during movement of the user; and defining the watershed pattern and the non-watershed pattern to energize tissues of the user to motivate interstitial fluid flow and to smooth cellulite.

BRIEF DESCRIPTION OF THE DRAWINGS

So that the above recited features and advantages of the present disclosure can be understood in detail, a more particular description of the invention, briefly summarized above, may be had by reference to the embodiments thereof that are illustrated in the appended drawings. The appended drawings illustrate example embodiments and are, therefore, not to be considered limiting of its scope. The figures are not necessarily to scale, and certain features and certain views of the figures may be shown exaggerated in scale or in schematic in the interest of clarity and conciseness.

FIGS. 6A-6M are schematic diagrams depicting the energizing garment with watershed and massage fingers arranged in various patterns.

FIGS. 8A-8C are schematic diagrams showing a user wearing the energizing garment before, during, and after exercise, respectively.

DETAILED DESCRIPTION

Figure 1:
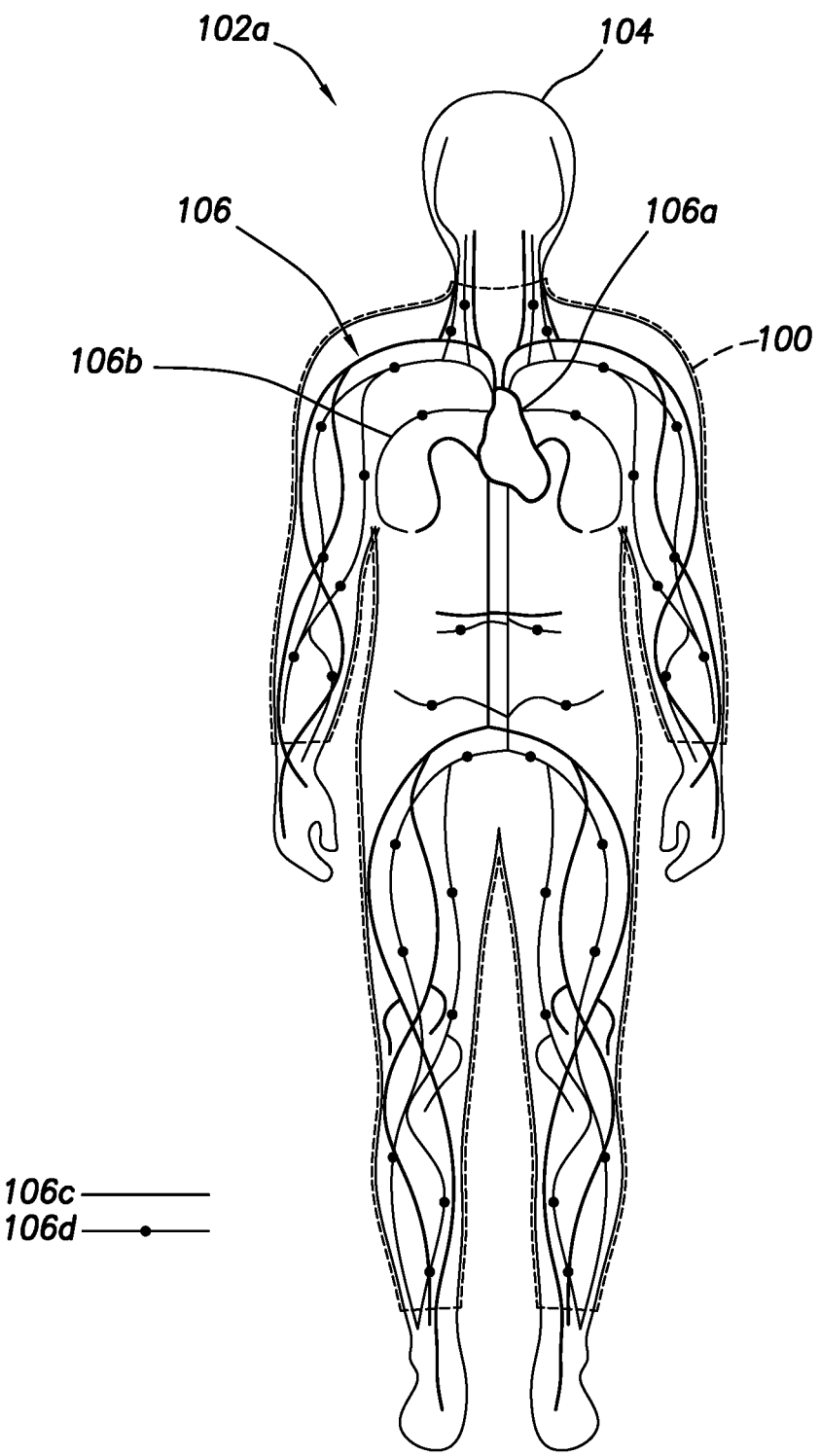
FIG. 1 is a schematic diagram depicting a pulmonary system of a user wearing an energizing garment.

The description that follows includes exemplary apparatus, methods, techniques, and/or instruction sequences that embody a solution related to garments for treating human tissues and/or encouraging fluid flow through the body. However, it is understood that the described embodiments may be practiced without these specific details.

Various devices, techniques, and surgical treatments have been developed to facilitate function of the vascular circulatory system and thereby improve overall health. For example, circulation devices, such as support hose, have been developed to address circulation conditions, such as varicose veins. In another example, aesthetic devices and treatments have been developed for aesthetic purposes, such as to reduce the appearance of fat or gynoid lipodystrophy (GLD), commonly known as "cellulite". GLD is a structural, inflammatory, and biochemical disorder of the subcutaneous tissue causing alterations in the topography of the skin. GLD affects 80-90% of post-pubertal women and is more evident in women over 30 years old. GLD is a complex and multifactorial condition that includes triggering, perpetuating, and exacerbating factors. It may be the result of structural, biochemical, metabolic, inflammatory, and morphological alterations, but a unique etiopathogenic explanation has not yet been determined. Examples of techniques aimed at addressing circulation conditions or reducing the appearance of fat or GLD are provided in Patent/Application Nos. WO2013190201, DE19825693, US20110191931, US2015366735, US20140142614, US2014148741, US20120089058, US2008208296, U.S. Pat. Nos. 5,794,266, 6,596,289, 9,756,881, 7,135,007, 4,810,559, 4,121,582, 6,138,281, 6,032,296, the entire contents of which are hereby incorporated by reference herein.

Despite the advancements in circulation and aesthetic technology, there remains a need for techniques capable of effectively treating tissues and/or encouraging fluid flow through the body (e.g., stimulating lymphatic drainage). The present disclosure is directed at providing such needs. More particularly, but not by way of limitation, the present disclosure relates to energizing garments wearable by a user. The energizing garment is provided with compressive material and fingers (e.g., watershed fingers and/or massage (non-watershed) fingers) that can be positioned about the user's body to provide a combination of compression and penetrating massage to tissues that are oriented relative to watersheds of the user. The compressive material and fingers may be sized, shaped, oriented, or arranged in patterns to strategically energize the tissues of the user to release fluids, such as lymph, interstitial fluids, and/or blood, along or across the watersheds.

The energizing garment may be designed with the intent of providing one or more of the following: enhance the function of the circulatory system; stimulate vascular circulation (e.g., localized microcirculation); simulate a manual lymphatic drainage massage; increase interstitial fluid absorption; facilitate release of lymph from tissues; promote displacement of lymph about (e.g., along or across) the watersheds of the user from one zone of the lymphatic system to another zone; reduce the accumulation of lymph in the lymphatic system; re-align the connective tissue in the dermis and hypodermis; enhance muscle recovery; smooth the texture of the skin surface; increase production of the vasodilator hormone, adiponectin; stimulate collagen and elastin production; improve skin elasticity; reduce the volume of fat tissues; shape and/or slim portions of the user's body (e.g., reduce thigh circumference); reduce the appearance of GLD; exfoliation; micro-dermabrasion; evacuation of toxins; and the like.

The effectiveness of the energizing garment on treating tissues of the user may be further enhanced during movement (e.g., physical exercise) as the compressive material compresses the fingers to agitate against the user, thereby affecting the user's skin and subcutaneous tissues. Movement of the user when combined with the compressive force of the material and agitation of the fingers relative to a watershed of the user combines to effectuate enhanced fluid flow through tissues. This combination of items may assist in tackling lipogenesis (increase of fat cells) due to a sedentary life style. Exercise in a variety of sports may be enhanced by combining massage and oriented fluid flow to and through watersheds with physical movement. Even at rest or at minimal movement, the user may benefit from the targeted treatment.

The energizing garment seeks to treat tissues of the user by encouraging displacement and flow of lymph in and through lymphatic vessels. The energizing garment uses non-invasive, penetrating engagement of the fingers under compression by the compressive material against the user's skin. When the energizing garment is worn, the fingers are positioned relative to watersheds of the user to engage the skin and agitate the subcutaneous tissues.

The energizing garment may be used to stimulate transport of fluids and nutrients through the lymphatic system. Lymphatic vessels are present in almost all human tissues and are richly supplied in tissues near the surface of the body, for example, the skin. In the skin, the arterial pulse pressure serves as a basic lymph transport mechanism. When the energizing garment is worn, the level of lymph flow generated by the arterial pulse pressure is enhanced by a combination of tissue massage (e.g., gentle maneuvering of the user's skin by engagement of the fingers in areas of the body that are oriented relative to watersheds of the user) and by elevation of the venous pressure (e.g., compressive force applied by the compressive material of the energizing garment).

The energizing garment seeks to activate the skin and underlying layers of connective tissue to stimulate fluid flow. The compressive material and/or fingers of the energizing garment are positioned in contact with the skin to affect the layers of the skin. The skin is composed of the epidermis (or surface epithelium), the dermis (an underlying layer of dense collagenous connective tissue that contains hair follicles, sweat glands, blood and lymphatic vessels, sensory receptors and nerves, and connective tissue cells), and the hypodermis (another connective tissue layer that is rich in white adipose cells and contains large blood vessels that supply the smaller vessels of the dermis).

The compressive material and/or fingers of the energizing garment apply force to the skin and agitate the skin in a way that impacts the epidermis, the dermis, and the hypodermis. The lymphatic system of the skin includes a network of lymphatic vessels that form two plexuses: the superficial plexus and the deep lymphatic plexus. The superficial plexus consists of thin vessels without valves and extends into the dermal papillae near the subpapillary arterial network. From the superficial plexus, branches drain into a series of larger lymphatic vessels in the lower dermis and the superficial zone of the subcutaneous tissue. The deep lymphatic plexus is situated below the second arterial network. Similar to the collecting venules of the lower dermis, the deep lymphatic vessels contain numerous valves. Blood vessels are found at the junction of the fat layer and the dermis and within the fat lobules. Lymphatic vessels are contained outside the subcutaneous adipose tissue. Although blood and lymphatic capillaries may lie immediately adjacent to each other they are generally believed to never anastomose.

Figure 2A:
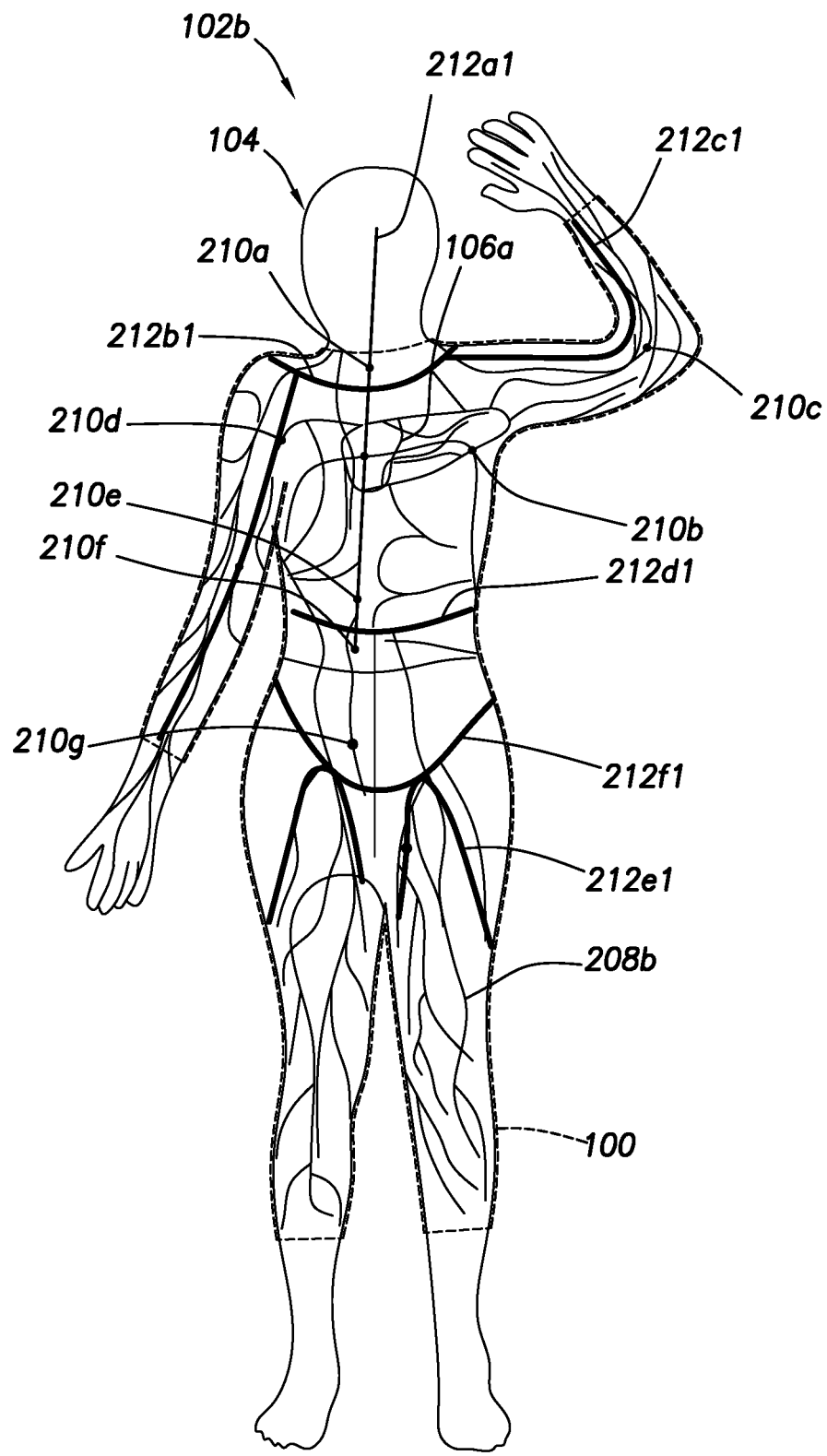
FIGS. 2A and 2B are schematic diagrams depicting anterior and posterior views, respectively, of a lymphatic system of the user wearing the energizing garment.
Figure 2B:
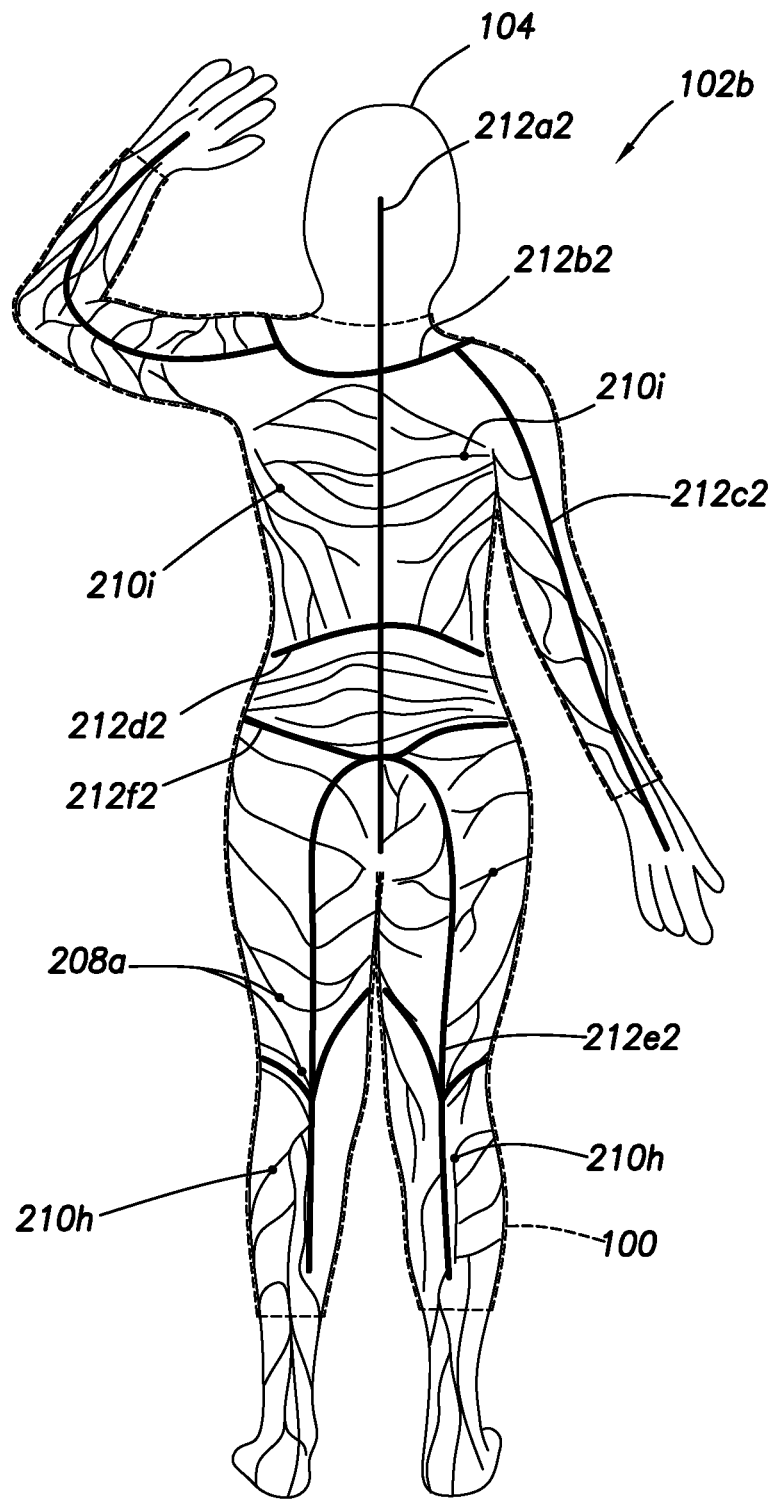

FIGS. 1, 2A and 2B are schematic diagrams depicting a circulatory system 102a and a lymphatic system 102b of a user 104 wearing the energizing garment 100. As shown in these views, the user 104 has a circulatory system 102a that includes a pulmonary system 106 for circulating blood and a lymphatic system 102b for circulating lymph through the body of the user 104. As shown in FIG. 1, the pulmonary system 106 includes a heart 106a, lungs 106b, veins 106c, and arteries 106d that form a loop for circulating blood through the body of the user 104. The heart 106a pumps the oxygenated blood via the arteries (and arterioles and capillaries) 106d to the organs of the body, and the veins (and venules) 106c return the blood to the heart 106a.

As shown in FIGS. 2A and 2B, the lymphatic system 102b includes a network of lymphatic vessels 208b. The network of lymphatic vessels 208b is composed of initial lymphatic capillaries that serve an absorptive role, collecting vessels that transport lymph between parts of the user 104, and lymph nodes 210a-i, or lymphoid organs. Lymph nodes are enclosed in a collagen-rich capsule, which is underlined with lymphatic endothelial cells forming the subcapsular sinus. The lymph nodes 210a-i include cervical 210a, auxiliary 210b, parasternal (mediastinal) 210c, cubital 210d, lumbar 210e, iliac 210f, inguinal 210g, popliteal 210h, and subscapular 210i nodes. There are estimated to be four hundred to seven hundred lymph nodes in the human body. Thus, additional lymph nodes, although not referenced, are also present about the user 104.

The lymphatic system 102b of the user 104 is shown in FIGS. 2A and 2B as being subdivided into two horizontal planes through the umbilicus and clavicles, and by a third plane vertically through the midline of the body. These planes are further subdivided into multiple zones (lymphatic tributary regions or non-watershed regions) delineated by watersheds 212a-e2. Each zone is an area where the lymph from the skin and subcutaneous tissue drains into a particular set of lymph nodes 210a-i.

The zones are generally separated by watersheds 212a-e2 occupied by small tortuous vessels forming an anastomosis between the lymphatic vessels of adjacent zones. Watersheds 212a1-e2 include: anterior and posterior sagittal (median) watershed regions 212a1,a2; anterior and posterior upper horizontal watershed 212b1,b2; tricipital watershed region 212c1,c2; anterior and posterior mid horizontal (transverse) watershed 212d1,d2; anterior and posterior chaps watershed region 212e1,e2; and, anterior and posterior lower horizontal (transverse) watershed 212f1,f2.

As also shown by FIGS. 1, 2A and 2B, the user 104 is wearing the energizing garment 100 over the upper and lower portions of the body. While specific configurations of the energizing garment 100 cover specific portions of the body as shown, it will be appreciated that one or more of the energizing garments 100 may be positioned over one or more regions of the body. For example, the energizing garment 100 may be a shirt, sleeve, pant, legging, leotard, sock, jumpsuit, leotard, bodysuit, band, belt, and/or other shape positionable about one or more regions of the body. Regardless of the shape of the energizing garment 100 or positioning on the body of the user 104, the energizing garment 100 of the present disclosure has features configured to treat tissues of the user 104 by promoting displacement of lymph about the watersheds 212a-e2 of the user 104 from one zone of the lymphatic system 102b to another zone.

Figure 3A:
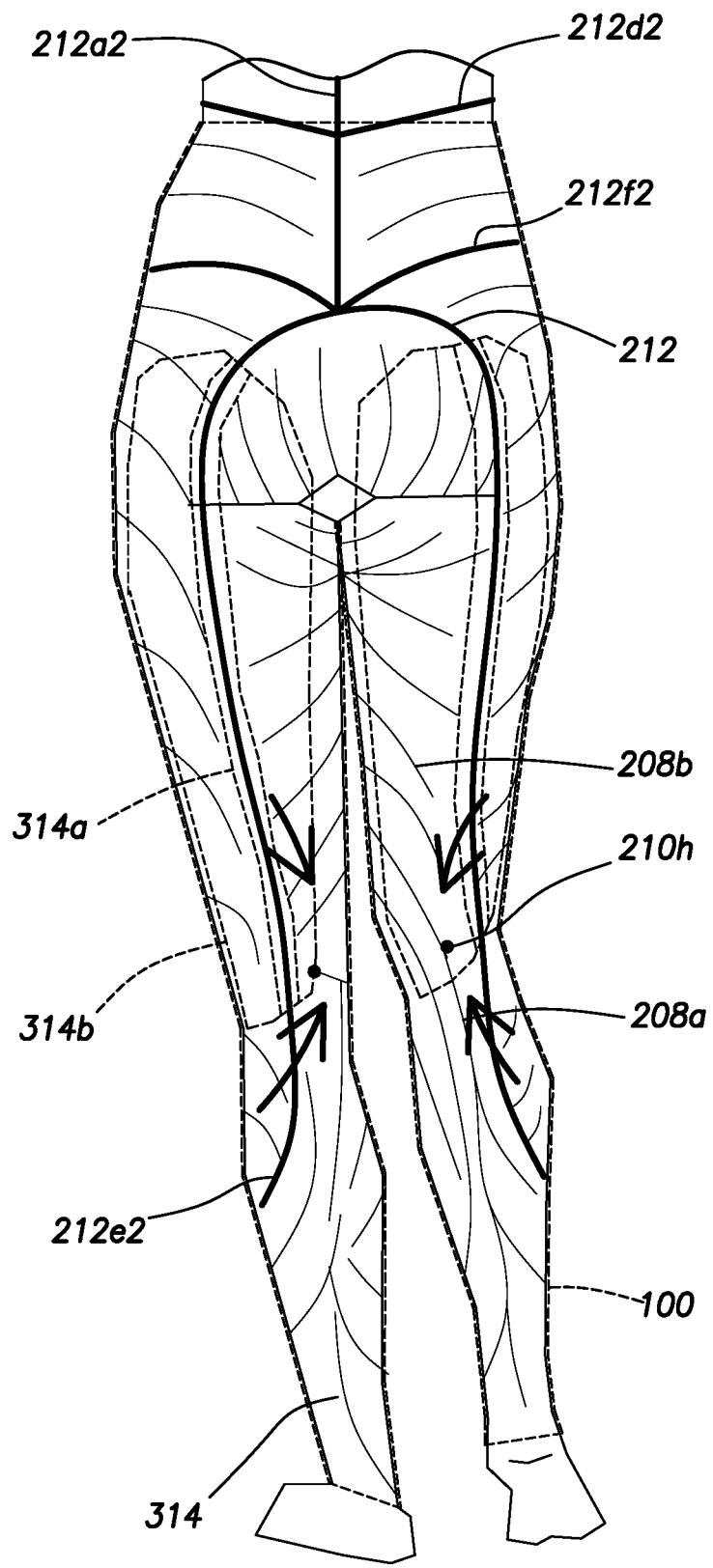
FIGS. 3A and 3B are schematic diagrams depicting anterior and posterior views, respectively, of a lower portion of the user wearing the energizing garment.
Figure 3B:
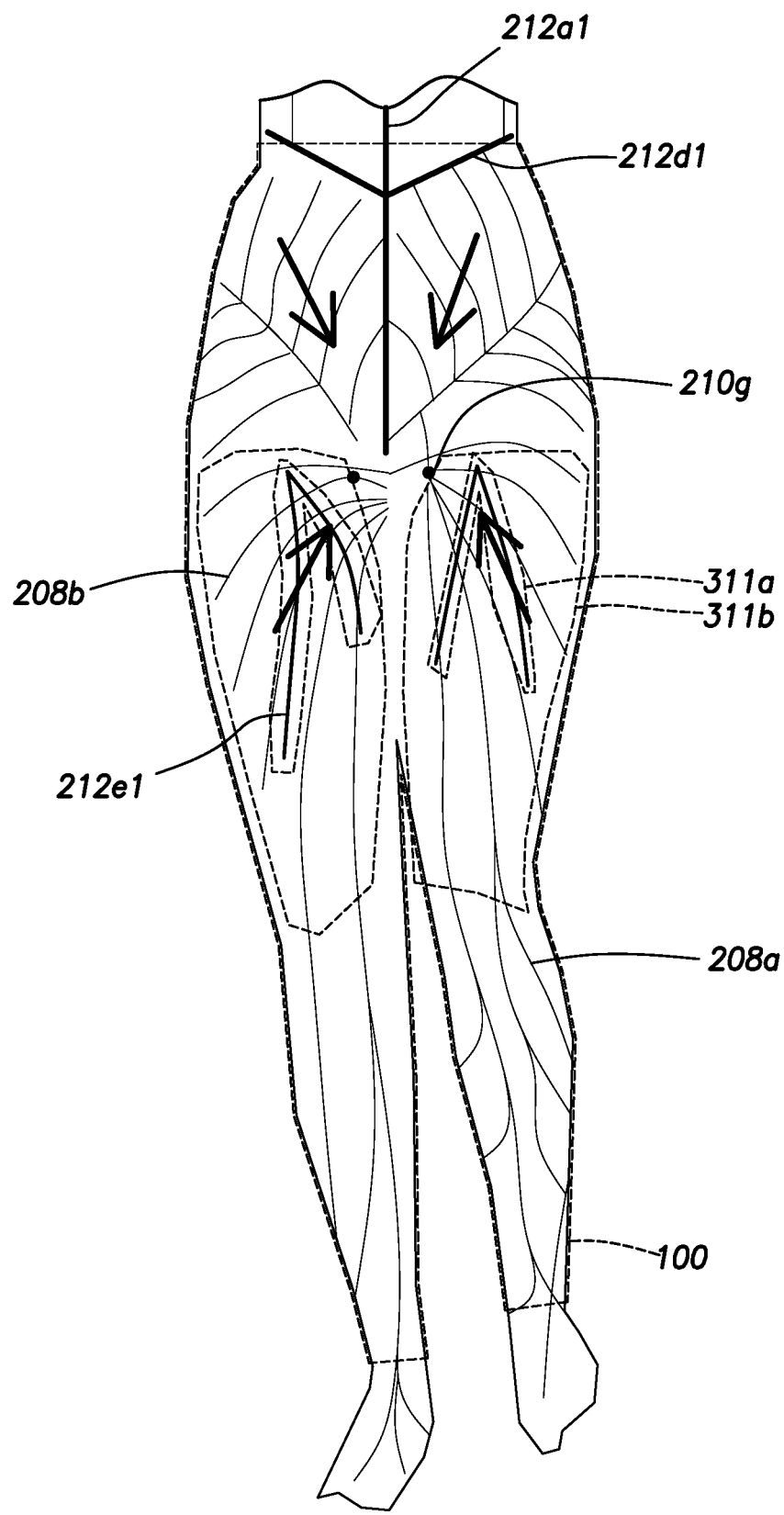

FIGS. 3A and 3B show various schematic depictions of lymphatic flow with respect to the watershed regions 212a1, a2,d1,d2,e1,e2 in the lower body portion of a user 104 wearing the energizing garment 100. These figures also depict a zone (or non-watershed region) 311b of the lower body of the user 104 and the network of lymphatic vessels 208b positioned therein that transport lymph along or across the watershed regions 212a1,a2,d1,d2,e1,e2, and then to one of the many lymph nodes in the body, for example, the inguinal lymph node 210g or the popliteal node 210h.

As shown in FIGS. 3A-3B, the energizing garment 100 extends over a lower portion of the body from a waist portion to an ankle portion of the user 104. The energizing garment 100 includes a compressive material (or fabric) 314 shaped to form pants or leggings worn by the user 104. Examples of compressive materials that may be used include cotton, nylon, spandex, elastane, polyamide, neoprene, plastics (e.g., polymers), and/or other fabrics or materials.

The compressive material may be, for example, a wearable material comprising a knitted elastic sleeve, casing, shell, sheath or similar material presenting an inner and an outer side. The compressive material may be a continuous or non-continuous material positionable on a desired area of the body, may have open areas where a portion of the wearer's skin on an area is uncovered, or have areas comprising a different fabric or material.

Figure 4:
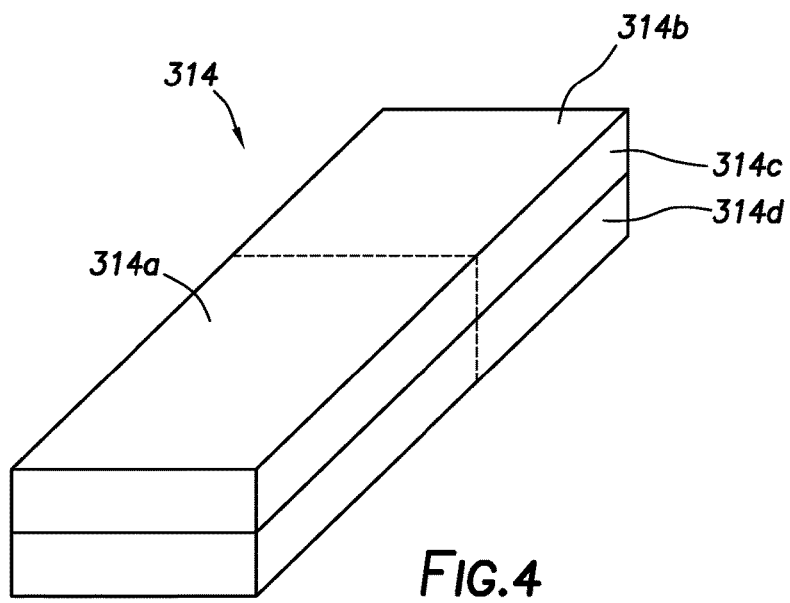
FIG. 4 is a schematic diagram of a compressive material of the energizing garment.

As shown in FIG. 4, the compressive material 314 may be a unitary compression material 314 or made of one or more portions, such as one or more pieces 314a,b and/or layers 314c,d joined together, for example, by sewing. The pieces 314a,b may be cut from the same integrally formed material, or formed from portions that are joined together. The layers 314c,d may be separate materials layered together or a coating or material applied to a base material. Additional layers of the same or different materials may be applied along portions of the compressive material 314 as support materials to further reinforce the compressive material 314.

The compressive material 314 may have an elasticity capable of applying pressure to portions of the body. When worn by the user 104, the compressive force exerted by the compressive material 314 may be graduated to encourage flow of lymph, interstitial fluids, blood and/or other fluids in the tissues of the user through the vascular circulatory system. For example, for an energizing garment 100 in the form of pants or leggings, the level of compression may decrease from an ankle portion to a knee portion to an upper thigh portion of the user 104. To further illustrate such example, an energizing garment 100 in the form of a pant or legging may be constructed with the levels of compression (measured in mmHg) as set forth in Table I below:

TABLE I

| GARMENT COMPRESSION LEVELS | | | |
| --- | --- | --- | --- |
| Example 1 | Example 2 | Example 3 | Example 4 |
| 8 = ankle | 12 = ankle | 18 = ankle | 23 = ankle |
| 8 = knee | 12 = knee | 15 = knee | 20 = knee |
| 6 = thigh | 10 = thigh | 12 = thigh | 12 = thigh |

Alternatively, the compressive material may have a compression effect that is relatively uniform when worn by the user 104, or a compression effect with an increasing degree of pressure from the distal end of a limb to its proximal end. Seams may be used along portions of the energizing garment 100, such as at the armpits, to allow for a gradient of pressure between parts of the body, such as between the elbow and the shoulder or other joints.

Compression may be defined based on Laplace's Law. According to Laplace's Law, the external pressure (P) exerted by an elastic casing, shell, sheath or similar material, particularly a stocking on a desired area of the body, is directly proportional to the tension (T) of the elastic casing, sheath, shell or similar, and inversely proportional to the curvature radius (r) of the casing, sheath, shell or similar in the mentioned area. Laplace's Law may be expressed by the formula:

$$P = T/r \qquad \text{Eq. (1)}$$

where (P) represents the pressure (g/cm2) exerted on the skin, (T) the tension (g/cm) of the elastic fabric, and (r) the curvature radius (cm) of the compressed area.

Laplace's Law may work well for portions of the body that have a generally cylindrical shape. The compression in these regions may be defined using Laplace's Law to provide desired compression. In portions of the body, such as thighs and/or buttocks, which may not have a generally cylindrical shape and/or have a higher radius of curvature, adjustments may be needed. In such cases, the elasticity of the compressive material may be increased/decreased as needed.

Referring back to FIGS. 3A and 3B, portions of the compressive material 314 may have the same or different content to provide various configurations of features. For example, portions of the compressive material 314 may be defined according to the watershed and non-watershed regions 311a,b, respectively of the user 104. In an example, the compressive material 314 along the watershed region 311a may have higher elasticity, increased thickness, and/or other features designed to engage or interact with the watershed region 311a, and portions of the compressive material 314 near the non-watershed region 311b may have lower elasticity, reduced thickness, and/or other features designed to engage or interact with the non-watershed region 311b. Additionally, portions of the compressive material 314 may be designed to interact together and/or with parts of the user 104 to provide a synergistic effect, such as enhanced circulation and/or enhanced lymph transport, for the user 104 as is described further herein.

Figure 5A:
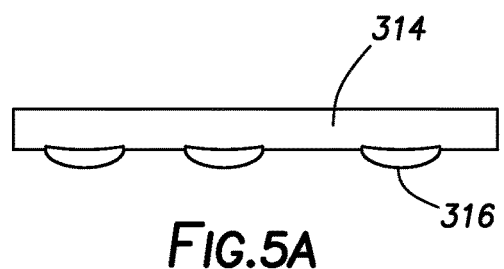
FIGS. 5A-5C are schematic diagrams depicting fingers positioned on the compressive material.
Figure 5B:
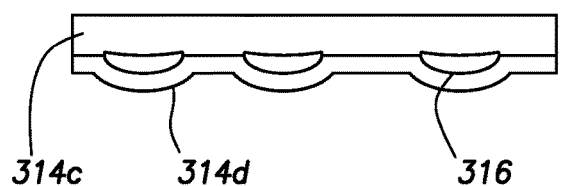
Figure 5C:
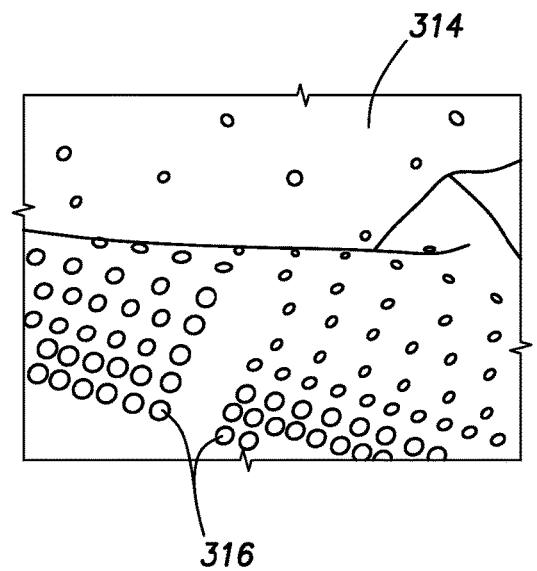

The energizing garment 100 may also include features to further activate the compressive material 314 and/or engage portions of the user 104 to further enhance operation of the compressive material 314 and/or the synergistic effects on the user 104. For example, as shown in FIGS. 5A-5C, fingers 316 may be positioned along one or more portions of the compressive material 314. The fingers 316 may be, for example, rigid members made of plastic (e.g., a polymer) or ceramic and integrated into or attached to the compressive material for engagement with the user 104.

As shown in FIG. 5A, one or more fingers 316 may be positioned along a skin side of the compressive material 314 for engagement with the user 104. The fingers may optionally be placed on an outer side of the garment along the body areas mainly affected by cellulite in order to improve the pressure on tissues during physical exercise on the floor. As shown in FIG. 5B, the fingers 316 may be positioned between layers 314c,d of the compressive material 314. The fingers 316 may have a variety of shapes and sizes (e.g., round, oval, polygonal, flat, rounded, pointed, symmetric, non-symmetric, etc.).

Various numbers and sizes of fingers may be used. For example, the fingers may be placed at intervals to allow airing and fluid flow through spaces between the fingers to prevent irritation or inflammation. The fingers may be, for example, under six millimeters (e.g., from about 0.5 to about 3 mm) in height, and have a diameter of from about 1 to about 3 times the height. The fingers may be arranged in patterns to achieve the desired compression and/or agitating force on the tissues.

The fingers 316 may comprise projections, protuberances, or other structures defining a bumpy composition. These fingers 316 may extend from an inner side of the energizing garment to apply a compressive force to a desired area. For example, when worn, the fingers 316 may be positioned along areas of the user that are prone to high fat or a higher concentration of GLD, such as against the user's skin along the thighs. The bumpy composition may alter the curvature of the energizing garment 100 locally when worn. This altered curvature may increase the compressive force in and immediately around the area of skin compressed by the fingers 316 when applied against the user 104, and will particularly be increased during high intensity movement.

The fingers 316 may be applied to the compressive material 314 in a variety of manners capable of preserving the bumpy configuration even after the garment is worn and the fabric stretched. The fingers 316 may be applied, for example, by printing a resin material or double-knitting a relatively hard material (e.g., higher durometer than the compressive material 314) on the compressive material 314 in raised deposits. The compressive material 314 or fingers 316 may optionally include far infrared qualities or contain active substances using micro encapsulation techniques (e.g., for cosmetic or hygienic purposes).

As shown in FIG. 5C, the fingers 316 may be located in predetermined patterns along the compressive material 314. The fingers 316 may be oriented towards the user and positioned along desired portions of the body. The fingers 316 may also be compressed against the skin when the garment 100 is worn to apply a force to tissues of the user 104. In an example, the fingers 316 may include watershed fingers positioned to apply a force to watershed region 311a (FIGS. 3A-3B) to encourage flow along or across the watershed, and the fingers 316 may include massage fingers 316b positioned to massage non-watershed region 311b (FIGS. 3A-3B) of the user 104 to encourage fluid flow towards or away from the watersheds as is described more fully herein.

Figure 6B:
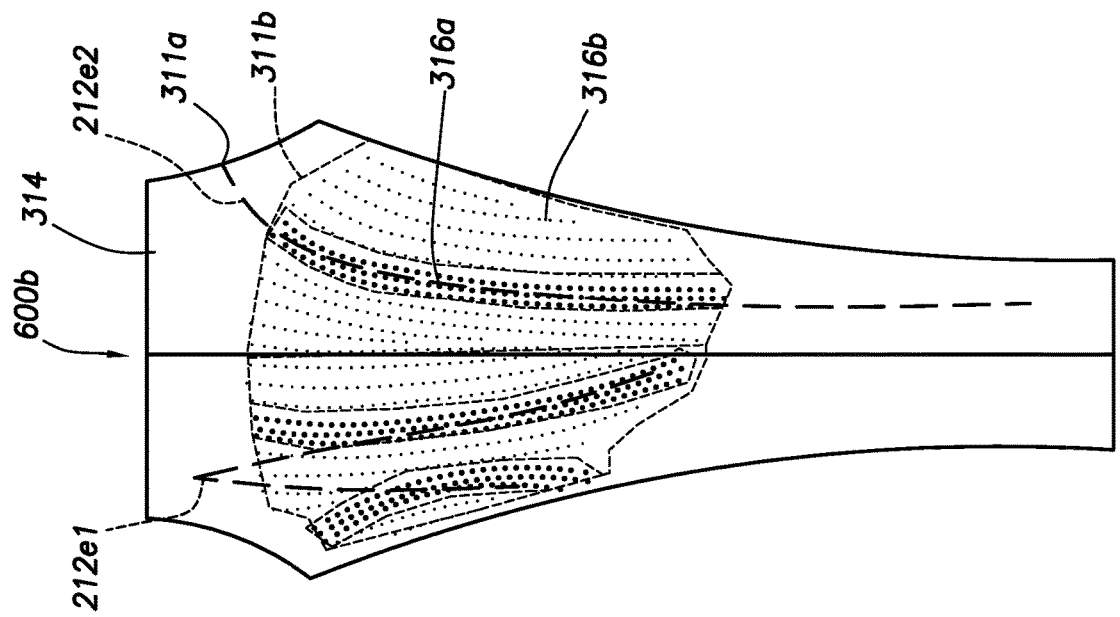

FIGS. 6A-6M depict example configurations of the energizing garment 100 including the compressive material 314, watershed fingers 316a, and massage fingers 316b wherein each figure depicts a different illustration of either a watershed pattern or massage pattern. FIGS. 6A-6G depict a portion of a pair of pants 600a-g; FIGS. 6H, 6J, and 6L depict a portion of a leotard 600h, 600j, and 600l, respectively; and, FIGS. 6I, 6K, and 6M depict a portion of an arm sleeve 600i, 600k, and 600m, respectively.

Referring specifically to FIGS. 6A-6G, each figure shows a pattern that may be used to form the pants 600a-d. Each of these pants 600a-d have an inseam, for example, portion of the pants 600a shown in FIG. 6A has inseams 618a1,a2 that may be sewn together to form a tubular shaped pant leg positionable on a leg of the user 104. An optional outer seam 618b is also shown. The portion of the pants 600a-d may be mated with a mirror image of the pants and joined at a mated front and rear seam to unite each portion into a unitary pair of the pants.

Figure 6A:
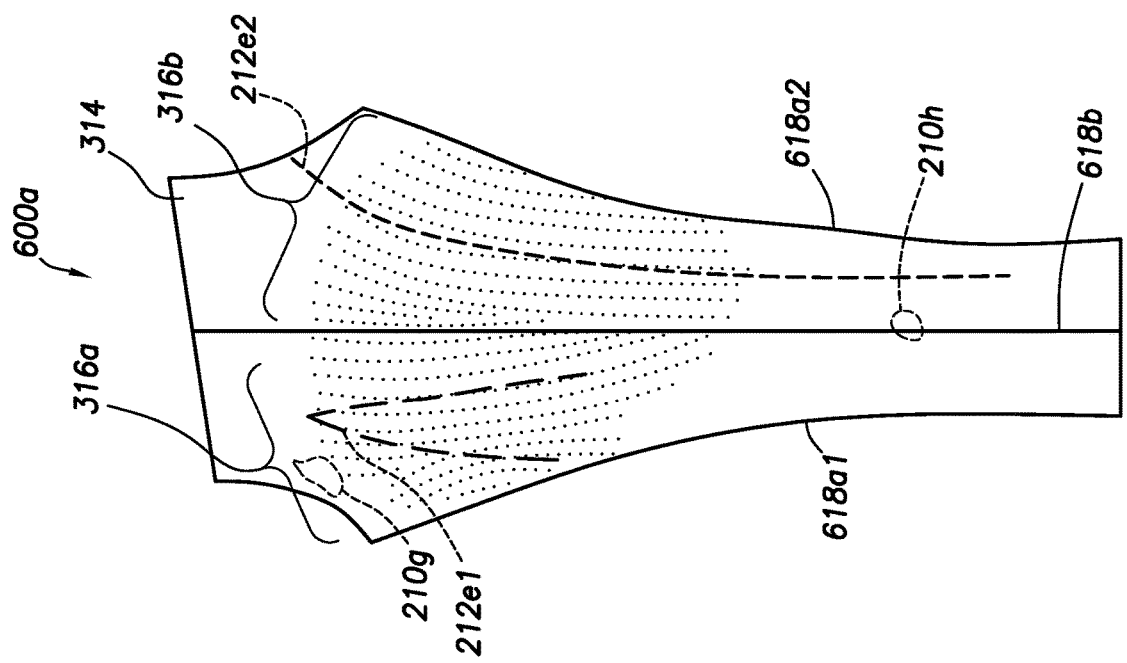

In the example of FIG. 6A, the portion of the pants 600a includes watershed fingers 316a arranged in a watershed pattern and massage fingers 316b arranged in a massage pattern. In this example, the watershed pattern and the massage pattern are generally aligned with the watershed regions 212e1,e2. While various combinations of various sizes and shapes of fingers 316a,b can be provided to steer the fluid in a desired direction, the watershed fingers 316a are illustrated in this example as generally being the same size and shape as the massage fingers 316b. The watershed and massage fingers 316a,b are positioned along the portion of the pants 600a in an upper thigh region of the user 104, a region where the lymphatic drainage and the vascular circulation may be low.

The watershed fingers 316a are arranged in a curved pattern that is generally aligned with the indicated watershed region 212e1 of a potential user, and the massage fingers 316b are arranged in a curved pattern that is generally aligned with another indicated watershed region 212e2. The watershed fingers 316a extend in linear columns along an inner surface of a front portion of the compressive material 314. The massage fingers 316b extend in linear columns along an inner surface of a rear portion of the compressive material 314. This pattern is shaped such that the compressive material 314 presses the fingers 316a,b against the user 104 to apply penetrating forces along the watershed region 212e1, and along linear lines a distance therefrom and parallel thereto. These penetrating forces energize the tissues of the user as described herein.

In the example of FIG. 6B, the watershed fingers 316a and massage fingers 316b are in a condensed configuration and generally aligned with the watershed regions 212e1,e2. The watershed fingers 316a are more densely placed along the indicated watershed regions 212e1,e2 of a potential user for engagement therewith. Such placement allows the watershed fingers 316a to apply a condensed compressive force along the watershed regions 212e1,e2 so as to simulate an effleurage (a form of massage involving a circular stroking movement made with the palm of the hand) over the watershed regions 212e1,e2 while wearing the energizing garment 100 during physical activity or exercise. The massage fingers 316b are generally positioned in the non-watershed region 311b for massaging engagement therewith. The massage fingers 316b are positioned in curvi-linear columns aligned with the shape of the watershed regions 212e1,e2. As shown by this figure, the massage fingers 316b may have a different shape, density and alignment to encourage fluid flow from the tissues of the user toward or away from the watershed regions 212e1,e2. The watershed fingers 316a may also define fluid channels that may be used to facilitate flow therebetween and drive fluid flow along or across the watershed regions 212e1,e2.

In the example of FIG. 6C, the watershed fingers 316a and massage fingers 316b are arranged in a condensed, tapered configuration relative to the watershed regions 212e1,e2. FIG. 6C is similar to FIG. 6B, except that the massage fingers 316b are in a different pattern along the non-watershed region 311b. In this example, the massage fingers 316b are arranged in curved columns on the compressive material 314 and tapered to generally conform to the shape of the indicated watershed regions 212e1,e2. These shapes orient the fluid pathways defined between the columns of massage fingers 316b to converge at or near intersections of the watershed regions 212e1,e2. These shapes also apply massaging force along tissues positioned a distance from the watershed regions 212e1,e2 to strategically energize the tissues of the user and enhance the transport of fluids along or across the watershed regions 212e1,e2.

In the example of FIG. 6D, the watershed fingers 316a and massage fingers 316b are in a condensed, angled configuration relative to the watershed regions 212e1,e2. FIG. 6D is also similar to FIG. 6B, except that the massage fingers 316b are in a different pattern along the non-watershed region 311b. A portion of the massage fingers 316b are in curved rows oriented towards the watershed regions 212e1, e2. These shapes orient the fluid pathways defined between the columns of massage fingers 316b that extend horizontally between the watershed regions 212e1,e2 to steer fluid flow toward or away from the watershed regions 212e1,e2. These shapes also apply massaging force along tissues positioned a distance from the watershed regions 212e1,e2.

This curved pattern may be defined such that the fingers 316a,b are penetratingly engaged against the skin of the user 104, applying a compressive force to the layers of subcutaneous connective tissues and the network of lymphatic vessels, thereby stimulating absorption and release of fluid therefrom. The curved pattern may also be shaped to define flow channels to encourage fluid flow along the curved pathways. The fluid may be encouraged to flow to the watershed regions 212e1,e2 and on to the inguinal lymph node 210g and the popliteal node 210h as schematically shown in FIG. 6A relative to the portion of the pants 600a.

Figure 6E:
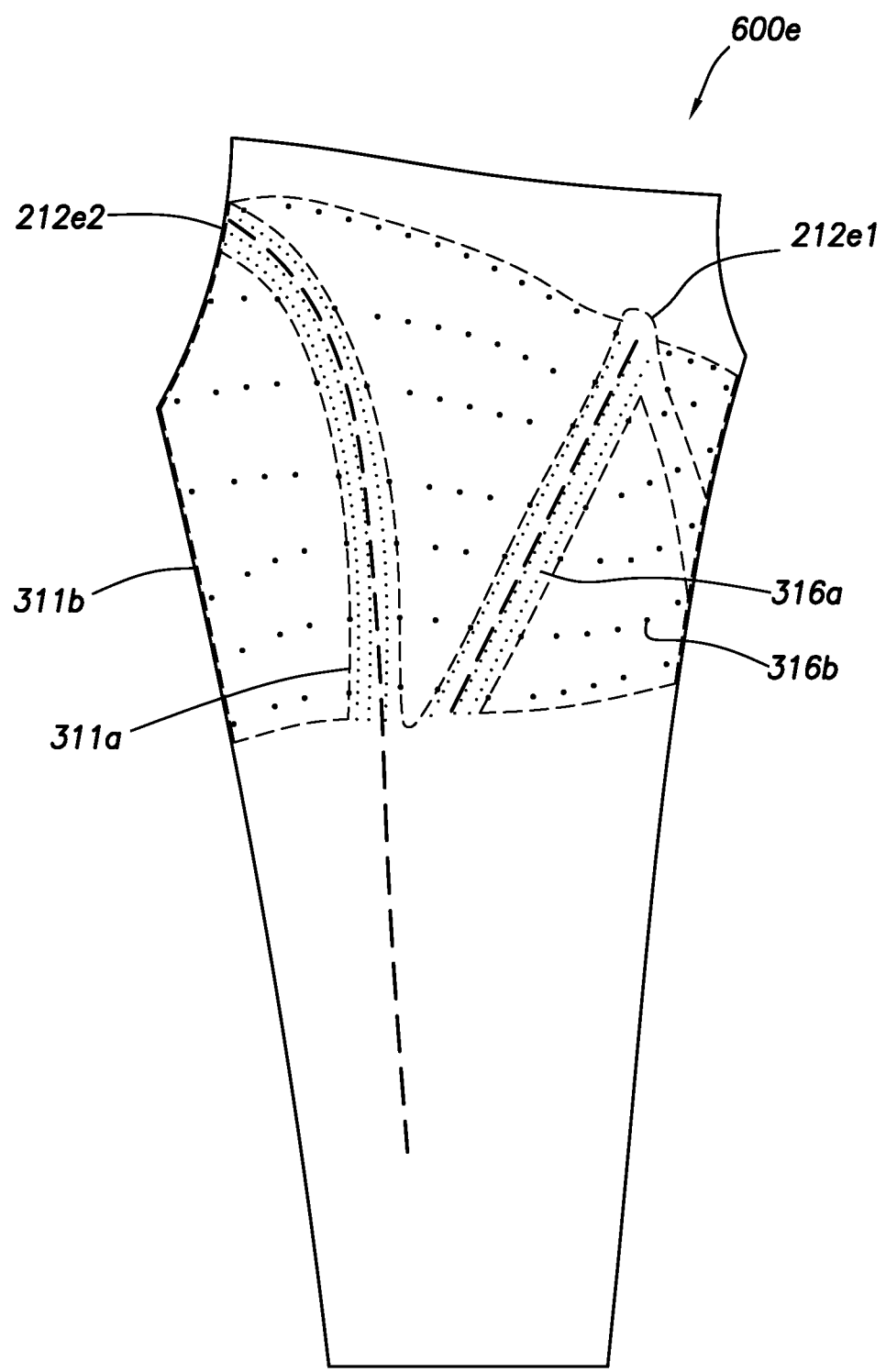
Figure 6I:
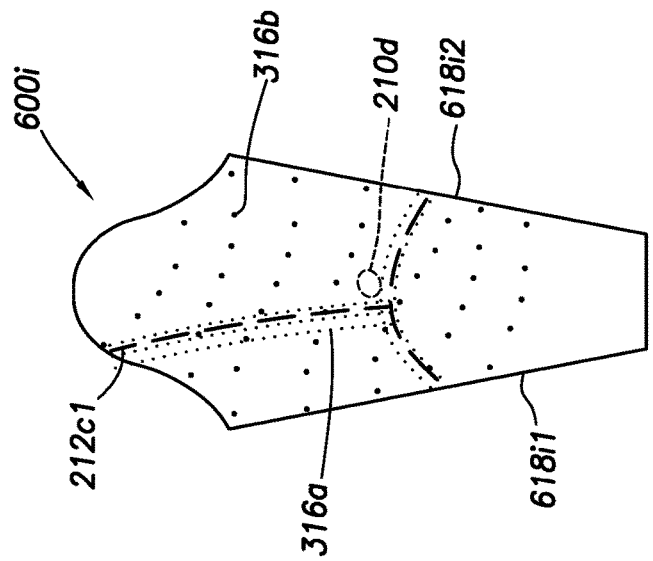
Figure 6H:
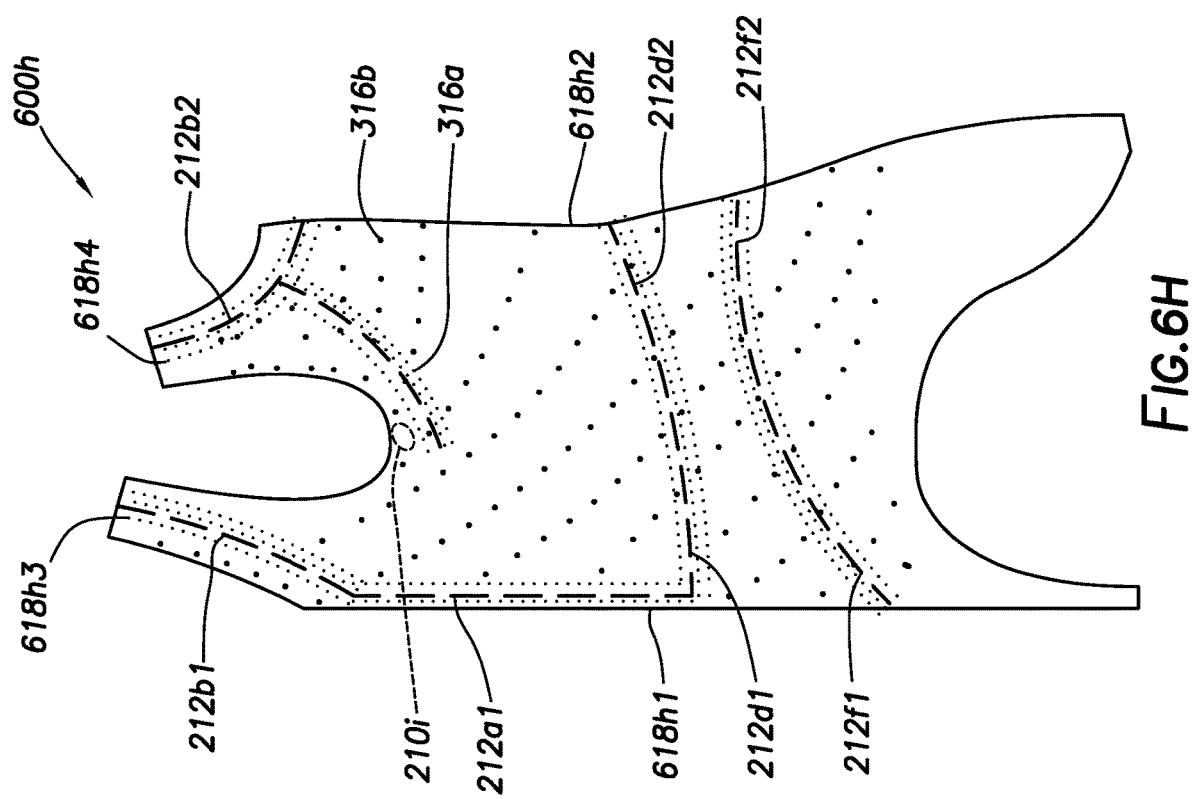
Figure 6M:
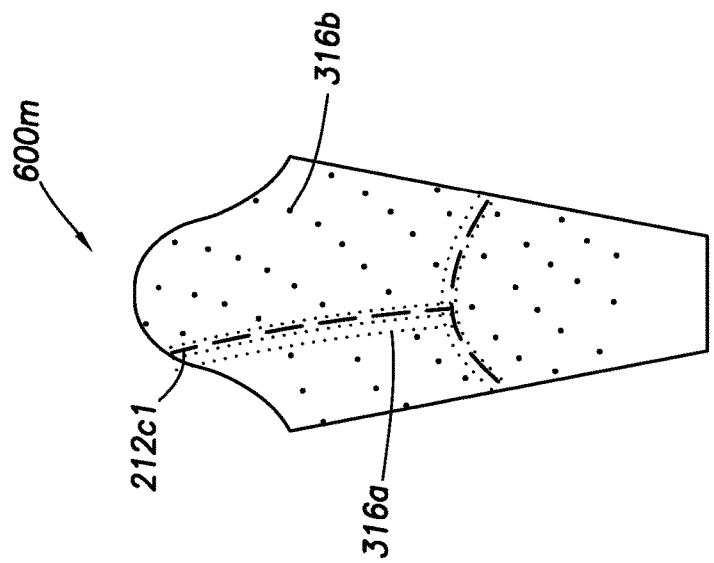
Figure 6L:
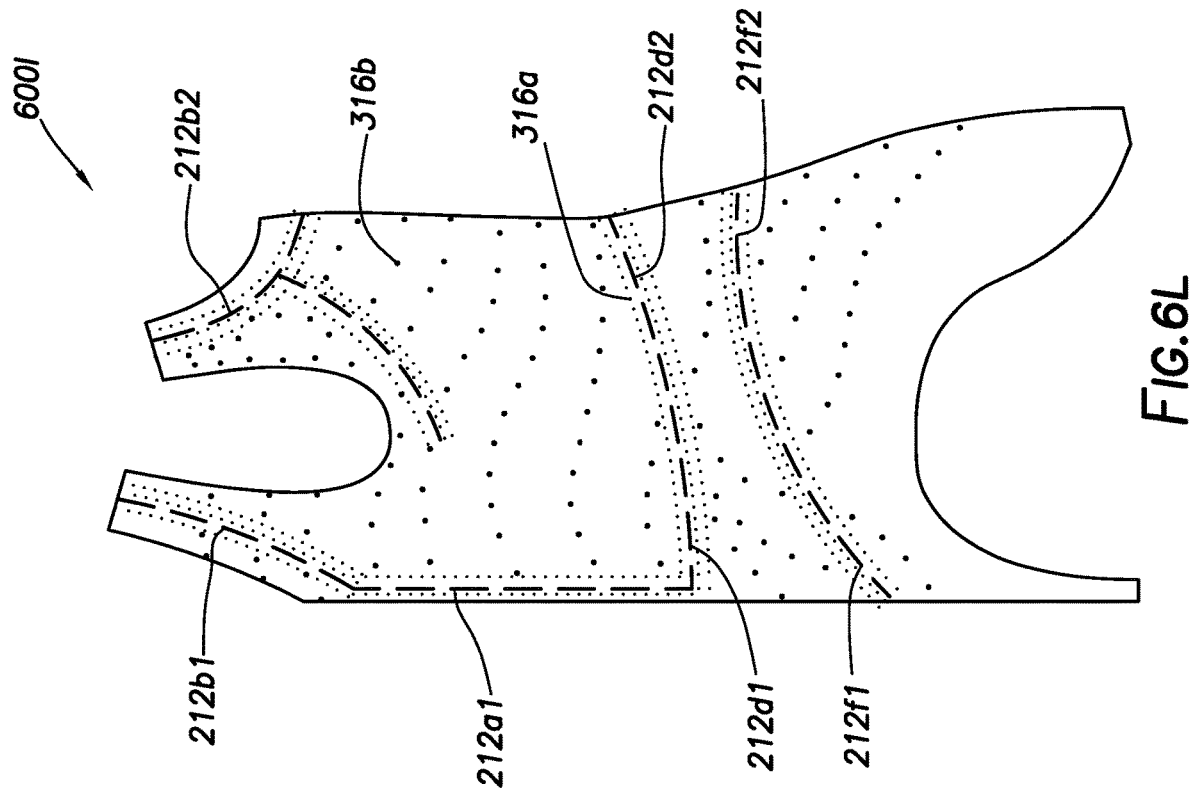

In the example of FIG. 6E, the watershed fingers 316a and massage fingers 316b are arranged in a cross-flow configuration wherein the massage fingers 316b extend across the watershed regions 212e1,e2 to steer fluid flow toward or away from the watershed regions 212e1,e2. As in FIG. 6B, the watershed fingers 316a are more densely placed along the indicated watershed regions 212e1,e2 of a potential user for engagement therewith. Such placement allows the watershed fingers 316a to apply a condensed compressive force along the watershed regions 212e1,e2 so as to simulate an effleurage over a portion of the watershed regions 212e1,e2. The penetrating massage of the fingers 316a,b energized by the compression of the compressive material 314 is intended to apply non-invasive pressure to subcutaneous tissues of the watershed regions 212e1,e2 to enhance lymphatic circulation and drainage in and near the watershed regions 212e1, e2, and thereby promoting flattening/smoothing of the skin texture and reducing the appearance of GLD.

Similar to the example depicted in FIG. 6E, the example portion of the pants depicted in FIGS. 6F and 6G also show the massage fingers 316b in an open, cross-flow configuration relative to the indicated watershed regions 212e1,e2. The massage fingers 316b are shown in each of FIGS. 6F and 6G to be arranged in curved rows, defining fluid pathways between each row of massage fingers 316b, to steer fluid flow toward or away from the watershed regions 212e1,e2.

Referring specifically to FIGS. 6H, 6J, and 6L, the energizing garment depicted therein is in the form of a leotard 600h, 600j, and 600l, respectively. Each of the leotards 600h,j,l have a seam, for example, portion of the leotard 600h shown in FIG. 6H has seams 618h1,h2 that may be mated with a mirror image of the portion of the leotard 600h and joined at a mated front seam 618h1 and rear seam 618h2 to form a close-fitting one-piece garment that generally covers the user's body from about the shoulders to about the top of the thigh.

In the examples of portions of the leotard 600h,j,l of FIGS. 6H, 6J, and 6L, each portion of the leotard 600h,j,l includes watershed fingers 316a arranged in a variety of watershed patterns, and massage fingers 316b secured to the non-watershed portion of the leotard 600h,j,l and arranged in a variety of massage patterns. The watershed fingers 316a and corresponding watershed pattern of the leotards 600h,j,l are densely placed along the indicated watershed regions 212a1,b1,b2,d1,d2,f1,f2 of a potential user for engagement therewith. The massage fingers 316b and corresponding massage patterns shown separately in each of FIGS. 6H, 6J, and 6L are oriented relative to the watershed regions 212a1, b1,b2,d1,d2,f1,f2 to define a fluid path for passage of fluid from the non-watershed region to at least one of the watershed regions 212a1,b1,b2,d1,d2,f1,f2 whereby tissues of the user 104 are energized to release fluid. The fluid may be encouraged to flow to the watershed regions 212a1,b1,b2, d1,d2,f1,f2 and on to the subscapular lymph node 210i as schematically shown in FIG. 6H relative to the portion of the leotard 600h.

Referring specifically to FIGS. 6I, 6K, and 6M, the energizing garment depicted therein is in the form of an arm sleeve 600i, 600k, and 600m, respectively. Each of the arm sleeves 600i,k,m has a seam, for example arm sleeve portion 600i shown in FIG. 6I has seams 618i1,i2 that may be sewn together to form a tubular shaped arm sleeve positionable on an arm of the user 104. Optionally, the arm sleeve 600i,k,m may be sewn to the leotard 600h,j,l to form a close-fitting one-piece garment that generally covers the arms and the core of the user 104.

In the examples of arm sleeve portions 600i,k,m of FIGS. 6I, 6K, and 6M, each arm sleeve portion 600i,k,m includes watershed fingers 316a arranged in a variety of watershed patterns, and massage fingers 316b secured to the non-watershed portion of the arm sleeves 600i,k,m and arranged in a variety of massage patterns. The watershed fingers 316a and corresponding watershed pattern of the arm sleeves 600i,k,m are densely placed along the indicated watershed region 212c1 of a potential user for engagement therewith. The massage fingers 316b and corresponding massage patterns shown separately in each of FIGS. 6I, 6K, and 6M are oriented relative to the watershed region 212c1 to define a fluid path for passage of fluid from the non-watershed region toward the watershed region 212c1, or define a fluid path for passage of fluid from the watershed region 212c1 toward an adjacent non-watershed region whereby tissues of the user 104 are energized to release fluid. The fluid may be encouraged to flow to the watershed regions 212c1 and on to the cubital lymph node 210d as schematically shown in FIG. 6i relative to the portion of the leotard 600i.

Figure 7A:
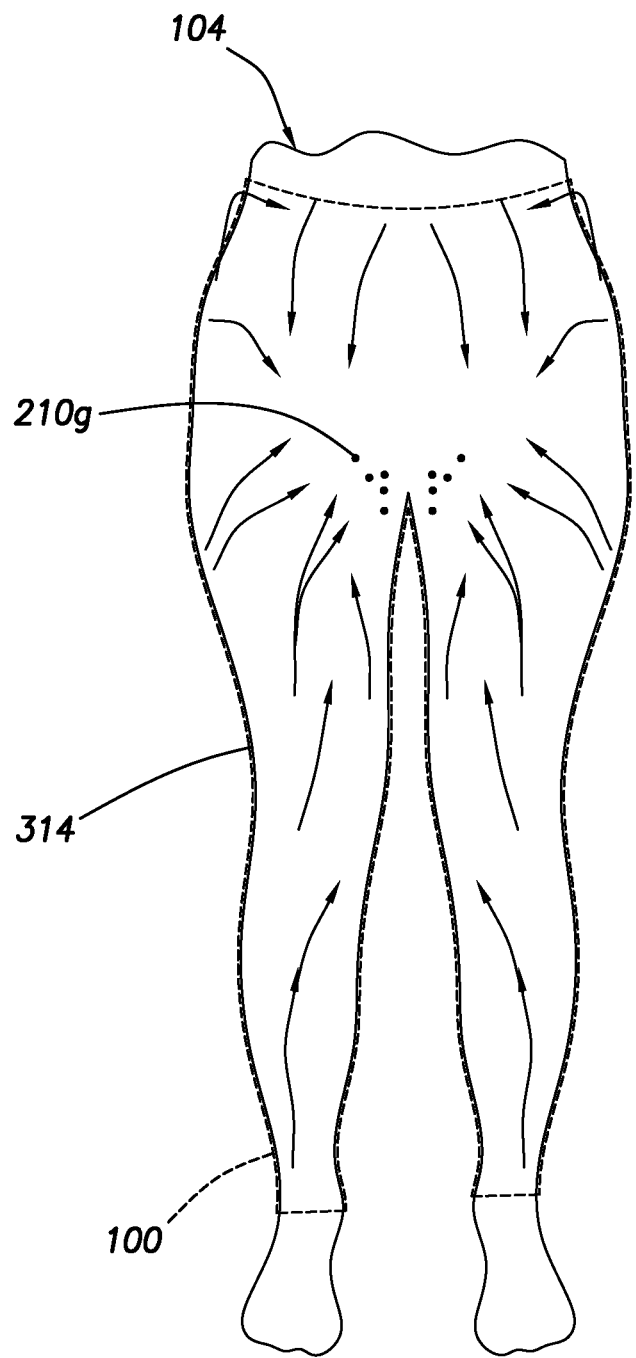
FIGS. 7A and 7B are schematic diagrams depicting flow of fluid through the user wearing the energizing garment during inactivity and activity, respectively.

FIGS. 7A-8C shows the effect of the energizing garment 100 on the user 104. FIG. 7A has arrows showing the compressive effect of the energizing garment 100. As shown by these arrows, the compressive force of the material can be defined to encourage flow of fluid through the body of the user 104. The compression may be defined such that a higher compression is in certain locations to steer the flow as indicated by the arrows. For example, the compressive material 314 may have a higher elasticity at a lower portion of the legs than an upper portion of the legs, thereby encouraging fluid flow upward along the legs and to the lymph nodes 210g as indicated by the arrows.

The fingers 316a,b may be applied to the material to penetratingly engage the skin and underlying tissues of the user, thereby enhancing the compressive effect of the energizing garment 100. Such compression is intended to energize the tissues and encourage them to release fluid. The fluid may pass along or across the watersheds and towards the lymph nodes.

Various combinations of materials, fingers, stiffness, compressibility, etc., can be provided to achieve the desired force and/or to steer the fluid in a desired direction. The fingers 316a,b may be provided with a shape, depth, stiffness, etc. such that when applied to the compressive material 314 and compressed against the user 104, the fingers 316a,b penetratingly engage the skin and underlying tissues. The fingers 316a,b may be shaped to provide an increased depth of the compressive material. A group of fingers may increase compression to regions of the body. The fingers 316a,b may have a rigidity that, when pressed against the user, increases the compressive force of the compressive material 314 and penetrates into the user's tissues.

The garment 100 may be provided with additional compression (e.g., by adding fingers 316a,b) to apply an additional compressive force in certain locations along the body. The fingers 316a,b may be secured along portions of the compressive material 314 to further treat the tissues of the user 104. For example, the fingers 316a,b may be placed in locations where increased compression is needed. Some portions of the body may have certain factors, such as tissue density, increased fat deposits, cellulite, etc., which may cause a need for increased/decreased compression. For example, an increase in compression may be provided along the thigh region where tissues may retain water and/or form undesirable dimpling in the skin. In such cases, the compression of the garment may be increased to a higher elasticity to provide added compression.

Figure 7B:
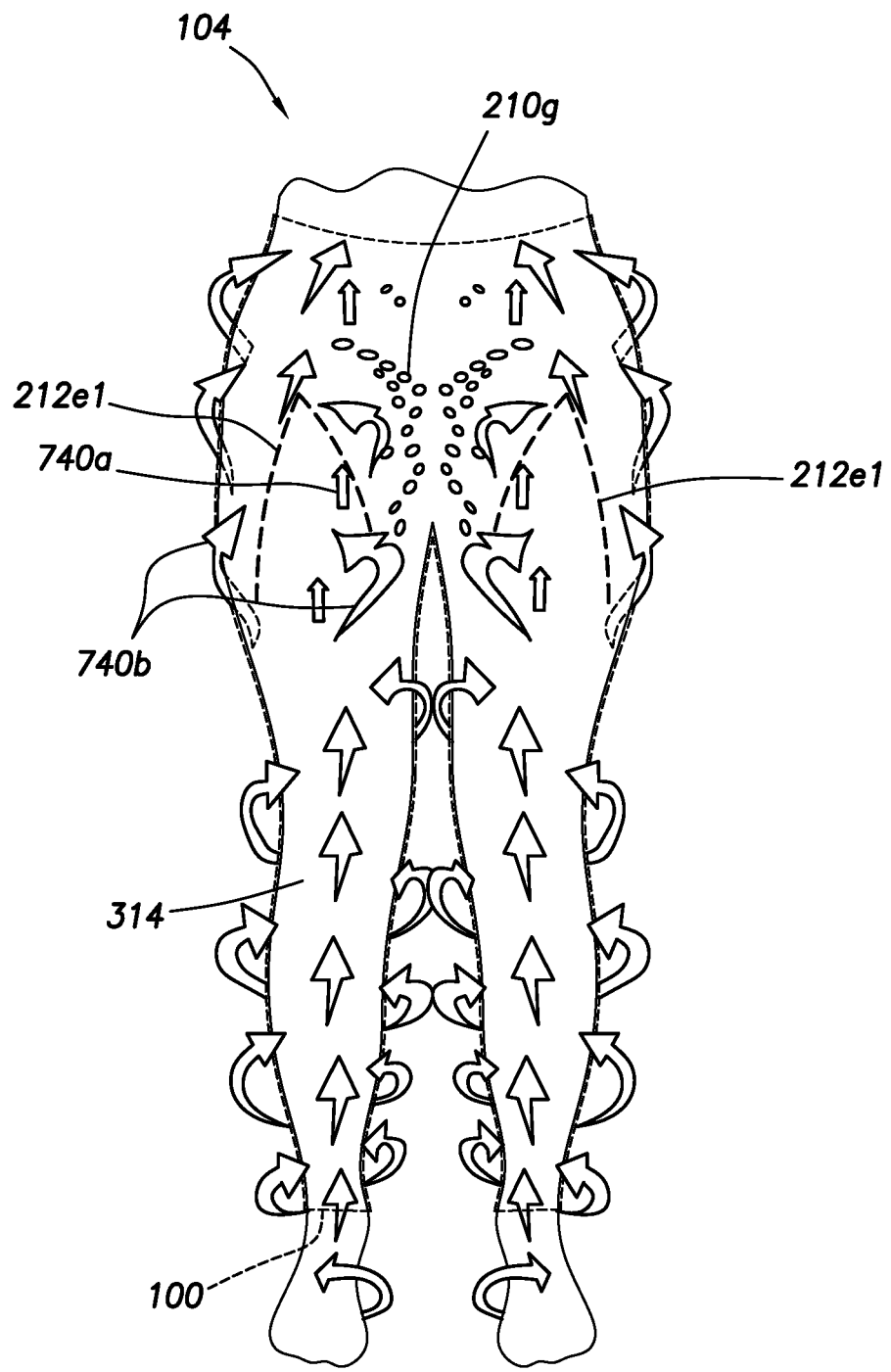

As shown by FIG. 7B, during movement, the fingers 316a,b may maneuver the tissues, thereby agitating layers of cells under the skin and providing a massaging effect while also compressing against the skin and into the tissues. Various combinations of materials, fingers, stiffness, compressibility, etc., can be provided to achieve the desired force and/or to steer the fluid in a desired direction during movement. The fingers 316a,b may be provided with a shape, depth, stiffness, etc. such that when applied to the compressive material 314 and moved about the skin during movement, the tissues are agitated as the fingers are compressed against the user 104 and penetratingly engage the skin and underlying tissues.

Referring to FIGS. 3A-3B, 6A-6M and 7A-7B, the energizing garment 100 (e.g., orientation of the fingers 316a,b as in FIGS. 6A-6M) may be designed to encourage fluid flow about the watersheds 212 and to the lymph nodes 210. In these examples, the watershed fingers 316a encourage flow along or across the watershed 212 (indicated in FIG. 7B by arrows 740a) and the massage fingers 316b encourage release of fluid from non-watershed portions and towards the watersheds 212 (indicated in FIG. 7B by arrows 740b).

Figure 8A:
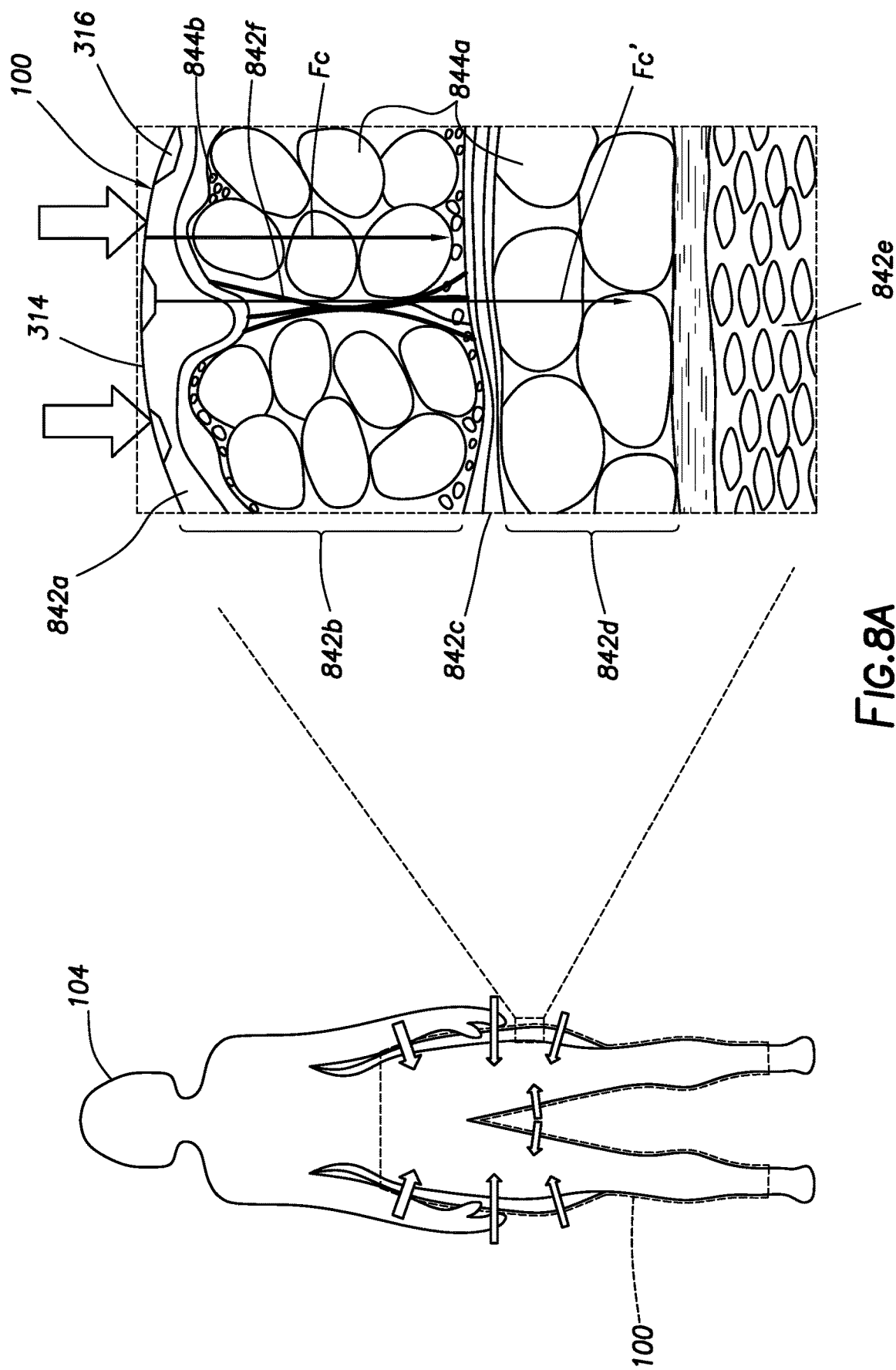
Figure 8C:
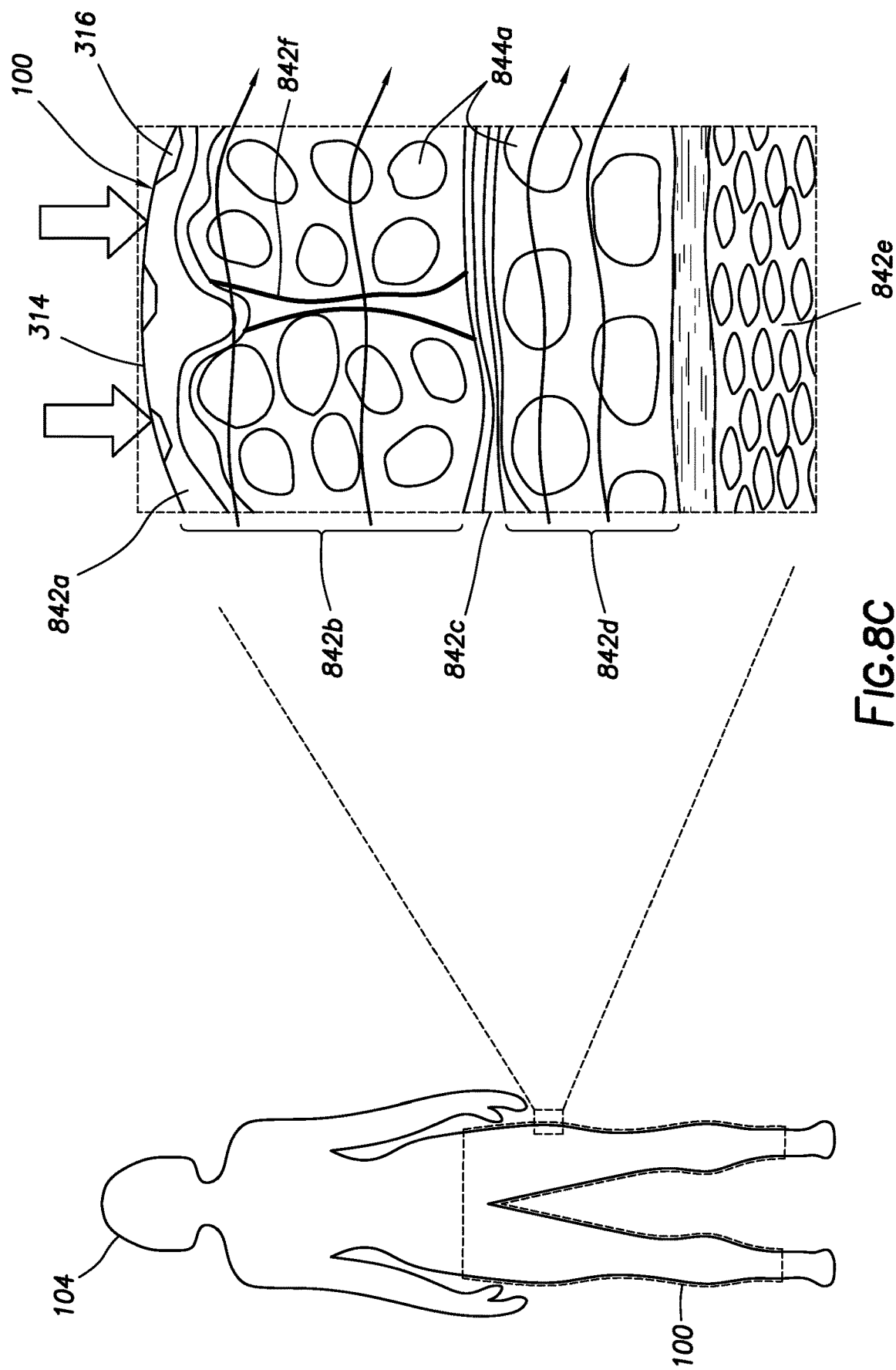

FIGS. 8A-8C show the user 104 before, during and after exercise, respectively, while wearing the energizing garment 100. As schematically depicted by these figures, the compressive material 314 and fingers 316 of the garment 100 may apply compressive force and a massaging action to engage and activate tissues to release fluid. The garment 100 engages tissues of the user 104 including skin 842a, outer layer (epidermis) 842b, facia superficialis (dermis) 842c, inner layer (hypodermis) 842d, muscle 842e, and connective tissue 842f. Fat cells 844a and fat lobes 844b are disposed in the inner and outer layers 842b,d.

As shown in FIG. 8A, before exercise, the garment 100 may apply a compressive force (Fc) against the user 104. This force may press against the skin 842a. The addition of fingers 316 may increase this compressive force to (Fc').

As shown in FIG. 8B, during exercise, the garment 100 moves with the user 104 such that the fingers 316 move back and forth against the skin 842a. The garment 100 remains under compression as indicated by the downward arrows. The movement of the fingers 316 under compression results in agitation of the tissues as indicated by the wavy arrows. This agitation further encourages release of fluid from the fat cells 844a as indicated by the curved arrows.

FIG. 8C shows the results of exercise with the garment 100. After exercise, the tissues of the user 104 have been compressed and smoothed. The fat cells 844a have shrunk, the connective tissue 842f has been broken down and/or strengthened, and the pockets of fat cells 844a have been reduced. Additional space is defined between the fat cells which provides a pathway for free passage of fluid through the tissues as indicated by the wavy arrows. This additional space may facilitate flow of fluid through the tissues. The compression and massaging may be used to smooth the skin, break up fibers, and/or reduce the appearance of cellulite. Orientation of the fingers may be used to steer the flow of the fluids through the tissues, to the watersheds, and/or through the watersheds.

In an experimental study, an energizing garment 100 in the form of leggings is worn by seven healthy female subjects, between the ages of 30 and 50 years old, with cellulite on the upper third of thigh and buttocks. The energizing garment 100 used by each test subject is similar in construction and function as the energizing garment 100/600b referenced by FIGS. 3A, 3B, and 6B. The energizing garment 100 used by each test subject extended over a lower portion of the body from waist to ankle and included compressive material 314 and fingers (e.g., watershed fingers 316a and massage fingers 316b) that, when worn, are positioned about the subject's body to provide a combination of compression and penetrating massage to tissues that are oriented relative to watersheds of the subject. The compressive material 314 used in the study is constructed from polyamide and elastane, and is shaped to apply a higher level of compressive force at a distal portion of the user (e.g., the ankle) than at a proximal portion (e.g., the upper thigh). The watershed fingers 316a and massage fingers 316b of the energizing garment 100 used by each test subject is in a condensed configuration and are generally aligned with the watershed regions of the subject. The watershed fingers 316a are more densely placed along the indicated watershed regions 212e1,e2 of the test subject for engagement therewith to apply a condensed compressive force along the watershed regions 212e1,e2 so as to simulate an effleurage over the watershed regions 212e1,e2 of each subject.

Before participating in the study, each of the subjects participates in inclusion/exclusion criteria and provides their informed written consent and photograph release consent. For this study, over a 56-day period, the energizing garment is used 3 times a week, during routine training sessions of physical activity (e.g., walking, running, cycling, yoga, and the like), between 45 min to 1 h 30 for each training session. If the subject trains more than 3 times a week, the garment is not to be worn for the additional training sessions.

Figure 9B:
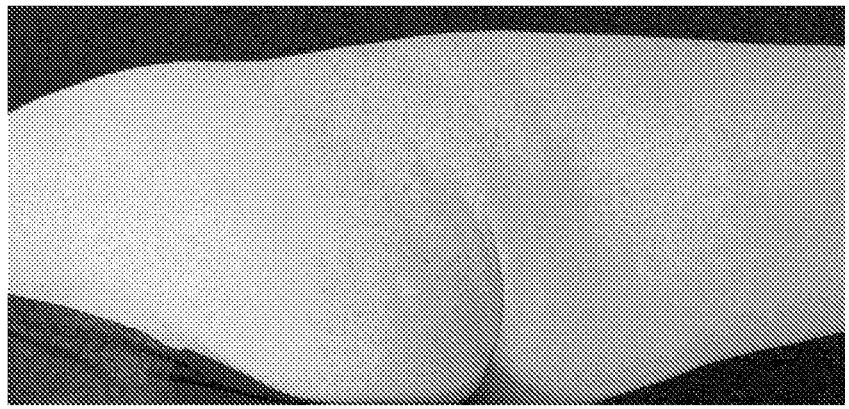
FIGS. 9A and 9B are photographs of a test subject at the beginning and end of an experimental study using the energizing garment.
Figure 9A:
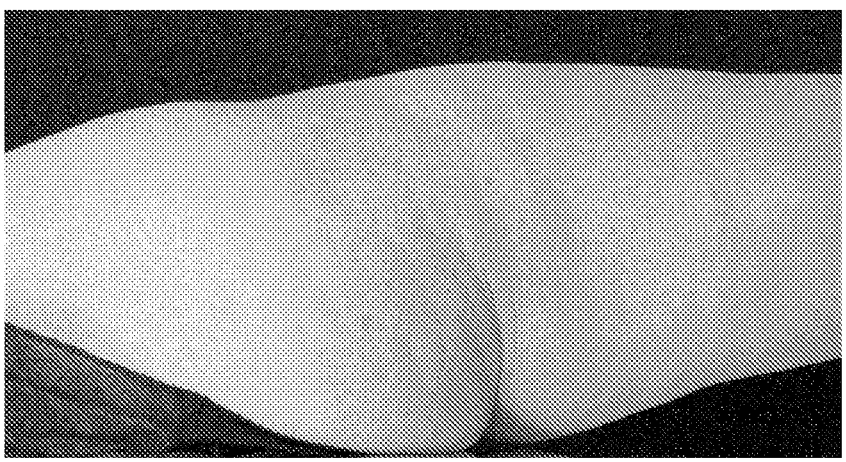

At T−0, prior to wearing the energizing garment, eleven photographs of each subject's thighs and buttocks are taken and inclusion/exclusion criteria is verified. FIG. 9A shows one photograph taken at T−0 of one such test subject.

At T+56, after wearing the energizing garment in accordance with the study guidelines, eleven additional photographs of each subject's thighs and buttocks are taken and inclusion/exclusion criteria is verified. FIG. 9B shows one photograph at T+56 of the same test subject depicted in FIG. 9A.

As shown in FIGS. 9A and 9B, visible appearance of cellulite is reduced between T−0 and T+56 after participating in the study in accordance with the test protocol. FIG. 9B, the photograph at T+56 shows a smoothing of the skin texture and a reduction in a surface area with depressions.

Figure 10:
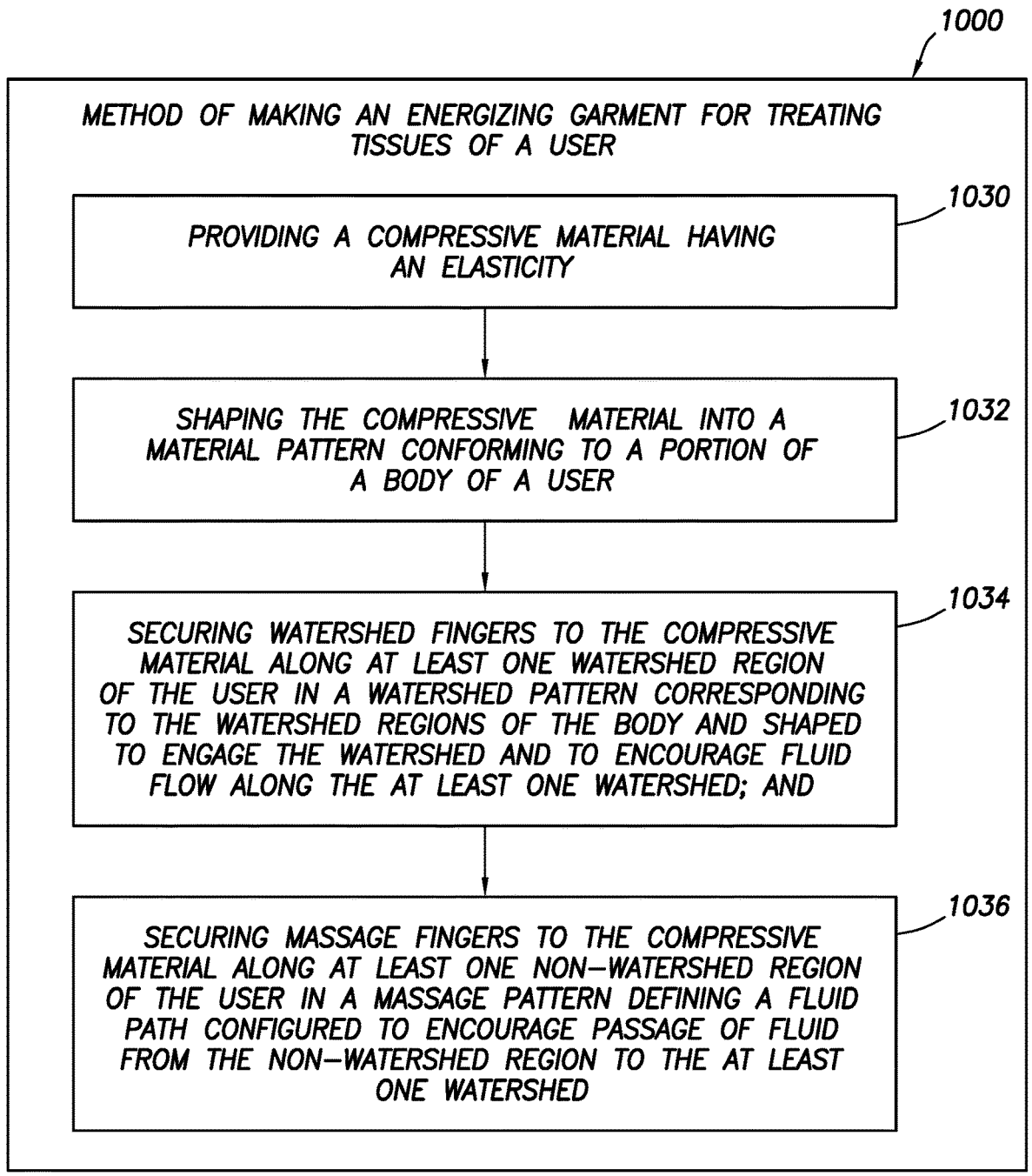
FIG. 10 is a flow chart depicting a method of making an energizing garment for treating tissues of a user.

FIG. 10 is a flow chart depicting a method 1000 of making an energizing garment for treating tissues of a user. The method involves 1030—providing a compressive material having an elasticity; 1032—shaping the compressive material into a material pattern conforming to a portion of a body of a user; 1034—securing watershed fingers to the compressive material along at least one watershed region of the user in a watershed pattern corresponding to the watershed regions of the body and shaped to engage the watershed and to encourage fluid flow along the at least one watershed; and 1036—securing massage fingers to the compressive material along at least one non-watershed region of the user in a massage pattern defining a fluid path configured to encourage passage of fluid from the non-watershed region to the at least one watershed.

The method may be performed in any order and repeated as desired.

While the embodiments are described with reference to various implementations and exploitations, it will be understood that these embodiments are illustrative and that the scope of the inventive subject matter is not limited to them. Many variations, modifications, additions and improvements are possible. For example, various combinations of one or more of the features and/or methods provided herein may be used. The fingers described herein may be positioned at various locations about the compressive material. For example, the watershed fingers may be secured to various locations about the compressive material and may map to one or more portions of one or more watershed regions. Similarly, the massage fingers may be secured to various locations about the compressive material and may map to one or more portions of one or more non-watershed regions. Various patterns of the watershed and/or the massage fingers may be arranged to provide the desired massage, the desired tissue treating effect, and the desired fluid flow toward or away from the watershed region. The fingers and compressive material may be sized, shaped, and/or strengthened to achieve the desired compressive force and agitation against the user's skin and underlying tissues.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter. For example, while certain garments are provided herein, it will be appreciated that various forms of garments, fabrics, materials, fingers, and/or other devices may be provided.

Insofar as the description above and the accompanying drawings disclose any additional subject matter that is not within the scope of the claim(s) herein, the inventions are not dedicated to the public and the right to file one or more applications to claim such additional invention is reserved. Although a very narrow claim may be presented herein, it should be recognized the scope of this invention is much broader than presented by the claim(s). Broader claims may be submitted in an application that claims the benefit of priority from this application.

What is claimed is:

1. A garment, comprising:
   a compressive material configured to be worn by a user, the compressive material shaped to apply a compressive force to skin of the user, the compressive material having at least one watershed portion to overlie at least one watershed of the user and at least one non-watershed portion to overlie at least one nonwatershed region of the user;
   watershed fingers secured to the at least one watershed portion of the compressive material, the watershed fingers arranged in a watershed pattern for orientation along at least a portion of the at least one watershed of the user to encourage fluid flow through the at least one watershed, the watershed pattern comprising curved, or curvi-linear lines of a plurality of watershed fingers for alignment along at least a portion of the at least one watershed of the user; and
   massage fingers secured to the at least one non-watershed portion of the compressive material for energizing tissues of a user to release fluid, the massage fingers arranged in a massage pattern comprising lines of massage fingers defining a fluid path therebetween for passage of the fluid from the at least one nonwatershed region, wherein:
the massage fingers have tips shaped to penetratingly massage the at least one nonwatershed region of the user;
the watershed and massage fingers are placed at intervals to allow fluid flow through spaces between the fingers;
the watershed fingers are more densely placed on the garment than the massage fingers.

2. The garment of claim 1, wherein the watershed pattern has a shape similar to the shape of the watershed.

3. The garment of claim 1, wherein the at least one watershed portion is to overlie at least two watersheds of the user and the watershed pattern comprises lines of watershed fingers for alignment along at least a portion each of the two watersheds of the user.

4. The garment of claim 3, wherein the at least two watersheds comprise an anterior and posterior chaps watershed.

5. The garment of claim 3, wherein the at least two watersheds comprise two watersheds selected from anterior sagittal watershed, anterior horizontal watersheds, mid horizontal watershed and posterior horizontal watershed.

6. The garment of claim 1, wherein the massage pattern is similar to the watershed pattern, the massage fingers positioned along the massage pattern a distance from the watershed.

7. The garment of claim 1, wherein the compressive material comprises material portions comprising at least one of multiple layers, multiple pieces patched together, integral portions, similar portions, at least one different portion, and combinations thereof.

8. The garment of claim 1, wherein the massage pattern is shaped to apply a compressive force to the at least one non-watershed region of the user.

9. The garment of claim 1, wherein the massage pattern is shaped to apply compressive forces to target areas of the user.

10. The garment of claim 1, wherein the massage fingers are positioned along target areas of the user comprising concentrations of cellulite, fat, muscle, veins, and combinations thereof.

11. The garment of claim 1, wherein the compressive material is shaped to form one of a shirt, pants, shorts, jumpsuit, and leotard.

12. The garment of claim 1, wherein the watershed fingers and massage fingers comprise rigid members.

13. The garment of claim 12, wherein the rigid members are made of plastic or ceramic.

14. The garment of claim 1, in which the compressive material is shaped to conform to a body of a user and the compressive material has an elasticity to apply a compressive force against the body of the user when worn by the user;
the watershed fingers are secured to the at least one watershed portion of the compressive material for compressively engaging at least a portion of the watershed of the user and to encourage flow through the at least one watershed; and
the massage fingers are secured to the at least one nonwatershed portion of the compressive material for massagingly engaging at least a portion of the at least one nonwatershed portion of the nonwatershed region of the user.

15. The garment of claim 14, wherein the massage fingers are positioned in a massage pattern defining a fluid pathway for encouraging the fluid flow towards the at least one watershed.

16. The garment of claim 14, wherein the massage fingers extend a distance below the compressive material to penetratingly engage the user and to compress layers below a surface of the skin of the user when the garment is worn.

17. The garment of claim 14, wherein the massage fingers comprise a plastic secured to the compressive material.

18. The garment of claim 14, wherein the massage fingers are positioned along one of: an inner surface of the compressive material, and between layers of the compressive material.

19. A method of making a garment for treating tissues of a user, the garment being as claimed in claim 1, the method comprising:
providing a compressive material having elasticity;
cutting the compressive material into a material pattern conforming to a body of the user such that, when worn by the user, the compressive material applies a compressive force against the body of the user and the compressive material has at least one watershed portion positioned to overlie least one watershed of the user and at least one non-watershed portion positioned to overlie least one nonwatershed region of the user;
securing watershed fingers to the compressive material in a watershed pattern; and
securing massage fingers to the compressive material in a nonwatershed pattern.

20. The method of claim 19, further comprising defining the material pattern such that the compressive material applies a compressive force against skin of the body.

21. The method of claim 19, further comprising defining the material pattern, the watershed pattern, and the nonwatershed pattern such that the compressive material applies a compressive force to drive the watershed fingers and the massage fingers against skin of the body and into the tissues underlying therebelow.

22. The method of claim 19, further comprising defining the material pattern, the watershed pattern, and the nonwatershed pattern defined such that the compressive material applies an energizing force to drive the watershed fingers and the massage fingers against skin of the body and agitate the tissues underlying therebelow during movement of the user.

23. The method of claim 19, further comprising defining the watershed pattern and the nonwatershed pattern to energize the tissues of the user to motivate interstitial fluid flow and to smooth cellulite.

* * * * *